US011166485B2

(12) United States Patent
Mua et al.

(10) Patent No.: US 11,166,485 B2
(45) Date of Patent: *Nov. 9, 2021

(54) PROTEIN-ENRICHED TOBACCO-DERIVED COMPOSITION

(71) Applicant: R.J. Reynolds Tobacco Company, Winston-Salem, NC (US)

(72) Inventors: John-Paul Mua, Advance, NC (US); Kyle Ford, Germanton, NC (US); Leigh Ann Blevins Joyce, Lewisville, NC (US); Margarette Elisa Lovette, Winston-Salem, NC (US); Joshua D. Morton, Evansville, IN (US); Leigh Hagan, Owensboro, KY (US); Barry Bratcher, Owensboro, KY (US); Samuel Mark Debusk, Lexington, NC (US)

(73) Assignee: R.J. Reynolds Tobacco Company, Winston-Salem, NC (US)

( * ) Notice: Subject to any disclaimer, the term of this patent is extended or adjusted under 35 U.S.C. 154(b) by 964 days.

This patent is subject to a terminal disclaimer.

(21) Appl. No.: 15/069,129

(22) Filed: Mar. 14, 2016

(65) Prior Publication Data

US 2016/0192697 A1    Jul. 7, 2016

Related U.S. Application Data

(63) Continuation of application No. 13/830,063, filed on Mar. 14, 2013, now Pat. No. 9,301,544.

(51) Int. Cl.
| | |
|---|---|
| *A23L 2/66* | (2006.01) |
| *A24B 15/24* | (2006.01) |
| *A61K 36/81* | (2006.01) |
| *A61K 8/64* | (2006.01) |
| *A61Q 19/00* | (2006.01) |
| *A61K 8/9789* | (2017.01) |
| *C07K 1/14* | (2006.01) |
| *C07K 14/415* | (2006.01) |

(52) U.S. Cl.
CPC .............. *A24B 15/241* (2013.01); *A23L 2/66* (2013.01); *A24B 15/24* (2013.01); *A61K 8/64* (2013.01); *A61K 8/9789* (2017.08); *A61K 36/81* (2013.01); *A61Q 19/00* (2013.01); *C07K 1/145* (2013.01); *C07K 14/415* (2013.01); *A61K 2236/00* (2013.01); *A61K 2800/10* (2013.01)

(58) Field of Classification Search
None
See application file for complete search history.

(56) References Cited

U.S. PATENT DOCUMENTS

| | | |
|---|---|---|
| 3,959,246 A | 5/1976 | Bickoff et al. |
| 4,244,381 A | 1/1981 | Lendvay |
| 4,268,632 A | 5/1981 | Wildman et al. |
| 4,340,676 A | 7/1982 | Bourque |
| 4,347,324 A | 8/1982 | Wildman et al. |
| 4,400,471 A | 8/1983 | Johal |
| 4,588,691 A | 5/1986 | Johal |
| 4,716,120 A | 12/1987 | Tsay et al. |
| 4,941,484 A | 7/1990 | Clapp et al. |
| 6,033,895 A | 3/2000 | Garger et al. |
| 7,048,211 B2 | 5/2006 | Bratcher et al. |
| 2006/0073333 A1 | 4/2006 | Anderson |
| 2006/0288449 A1 | 12/2006 | Garger et al. |
| 2007/0137663 A1 | 6/2007 | Taylor et al. |
| 2007/0193596 A1 | 8/2007 | Mori et al. |
| 2011/0174323 A1 | 7/2011 | Coleman, III et al. |
| 2011/0259353 A1 | 10/2011 | Coleman, III et al. |
| 2012/0141648 A1 | 6/2012 | Morton et al. |
| 2012/0152265 A1 | 6/2012 | Dube et al. |
| 2012/0192880 A1 | 8/2012 | Dube et al. |
| 2012/0192882 A1 | 8/2012 | Dube et al. |
| 2012/0211016 A1 | 8/2012 | Byrd, Jr. et al. |
| 2012/0272976 A1 | 11/2012 | Byrd et al. |

FOREIGN PATENT DOCUMENTS

| | | |
|---|---|---|
| CA | 1 166 114 | 4/1984 |
| CN | 1101942 | 4/1995 |
| CN | 101687906 | 3/2010 |

(Continued)

OTHER PUBLICATIONS

Millipore Sigma 2020 https://www.emdmillipore.com/US/en/life-science-research/chromatography-sample-preparation/membrane-learning-center/Pore-Size-or-NMWL.*

Krishnan et al., "A Rapid Method for Depletion of Rubisco From Soybean (Glycine Max) Leaf for Porteomic Analysis of Lower Abundance Proteins," *Phytochemistry*, 2009, pp. 1958-1964, vol. 70.

(Continued)

*Primary Examiner* — Terry A McKelvey
*Assistant Examiner* — Catheryne Chen
(74) *Attorney, Agent, or Firm* — Womble Bond Dickinson (US) LLP

(57) ABSTRACT

The present disclosure describes methods of obtaining and/or deriving proteins from plants of the *Nicotiana* species and methods for incorporation of such proteins into various products. For example, a method for obtaining a protein-enriched material from a plant of the *Nicotiana* species or portion thereof is provided, comprising: extracting one or more proteins from the plant material into a solvent to form a liquid protein-containing extract; separating a solid extracted plant material from the liquid protein-containing extract; clarifying the liquid protein-containing extract to form a clarified protein-containing extract and a solids fraction; and treating the clarified protein-containing extract so as to provide a protein-enriched material comprising at least about 60% protein by weight.

11 Claims, 4 Drawing Sheets

(56) References Cited

FOREIGN PATENT DOCUMENTS

| EP | 1 623 634 | 2/2006 |
|---|---|---|
| JP | 1162008 | 10/1997 |
| WO | WO 82/04066 | 11/1982 |
| WO | WO 2005/112670 | 12/2005 |
| WO | WO 2008/143914 | 11/2008 |

OTHER PUBLICATIONS

Siceloff, "A Revolutionary Upheaval? Tobacco for Protein" N.C. Insight, Jun. 1981, pp. 28-32. http://www.nccppr.org/drupal/content/insightarticle/918/tobacco-for-protein.

Hauck et al., "The Manufacture of Allergenic Extracts in North America," *Clinical Review in Allergy and Immunology*, 2001, pp. 93-110, vol. 21.

* cited by examiner

PROTEIN-ENRICHED TOBACCO-DERIVED COMPOSITION

CROSS-REFERENCE TO RELATED APPLICATIONS

The present application is a continuation of U.S. application Ser. No. 13/830,063, filed on Mar. 14, 2013, which is incorporated herein by reference in its entirety.

FIELD OF THE INVENTION

The present invention relates to products made or derived from tobacco, or that otherwise incorporate tobacco or components of tobacco, and are intended for human consumption. Of particular interest are ingredients or components obtained or derived from plants or portions of plants from the *Nicotiana* species.

BACKGROUND OF THE INVENTION

Cigarettes, cigars, and pipes are popular smoking articles that employ tobacco in various forms. Such smoking articles are employed by heating or burning tobacco to generate aerosol (e.g., smoke) that may be inhaled by the smoker. Popular smoking articles, such as cigarettes, have a substantially cylindrical rod shaped structure and include a charge, roll or column of smokable material such as shredded tobacco (e.g., in cut filler form) surrounded by a paper wrapper thereby forming a so-called "tobacco rod." Normally, a cigarette has a cylindrical filter element aligned in an end-to-end relationship with the tobacco rod. Typically, a filter element comprises plasticized cellulose acetate tow circumscribed by a paper material known as "plug wrap." Certain cigarettes incorporate a filter element having multiple segments, and one of those segments can comprise activated charcoal particles. Typically, the filter element is attached to one end of the tobacco rod using a circumscribing wrapping material known as "tipping paper." It also has become desirable to perforate the tipping material and plug wrap, in order to provide dilution of drawn mainstream smoke with ambient air. A cigarette is employed by a smoker by lighting one end thereof and burning the tobacco rod. The smoker then receives mainstream smoke into his/her mouth by drawing on the opposite end (e.g., the filter end) of the cigarette.

The tobacco used for cigarette manufacture is typically used in blended form. For example, certain popular tobacco blends, commonly referred to as "American blends," comprise mixtures of flue-cured tobacco, burley tobacco and Oriental tobacco, and in many cases, certain processed tobaccos, such as reconstituted tobacco and processed tobacco stems. The precise amount of each type of tobacco within a tobacco blend used for the manufacture of a particular cigarette brand varies from brand to brand. However, for many tobacco blends, flue-cured tobacco makes up a relatively large proportion of the blend, while Oriental tobacco makes up a relatively small proportion of the blend. See, for example, *Tobacco Encyclopedia*, Voges (Ed.) p. 44-45 (1984), Browne, *The Design of Cigarettes*, 3$^{rd}$ Ed., p. 43 (1990) and *Tobacco Production, Chemistry and Technology*, Davis et al. (Eds.) p. 346 (1999).

Tobacco also may be enjoyed in a so-called "smokeless" form. Particularly popular smokeless tobacco products are employed by inserting some form of processed tobacco or tobacco-containing formulation into the mouth of the user. See for example, the types of smokeless tobacco formulations, ingredients, and processing methodologies set forth in U.S. Pat. No. 1,376,586 to Schwartz; U.S. Pat. No. 3,696,917 to Levi; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,991,599 to Tibbetts; U.S. Pat. No. 4,987,907 to Townsend; U.S. Pat. No. 5,092,352 to Sprinkle, III et al.; U.S. Pat. No. 5,387,416 to White et al.; U.S. Pat. No. 6,668,839 to Williams; U.S. Pat. No. 6,834,654 to Williams; U.S. Pat. No. 6,953,040 to Atchley et al.; U.S. Pat. No. 7,032,601 to Atchley et al.; and U.S. Pat. No. 7,694,686 to Atchley et al.; US Pat. Pub. Nos. 2004/0020503 to Williams; 2005/0115580 to Quinter et al.; 2005/0244521 to Strickland et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0029117 to Mua et al.; 2008/0173317 to Robinson et al.; 2008/0196730 to Engstrom et al.; 2008/0209586 to Neilsen et al.; 2008/0305216 to Crawford et al.; 2009/0025738 to Mua et al.; 2009/0025739 to Brinkley et al.; 2009/0065013 to Essen et al.; 2009/0293889 to Kumar et al.; 2010/0018540 to Doolittle et al; 2010/0018541 to Gerardi et al.; 2010/0291245 to Gao et al; 2011/0139164 to Mua et al.; 2011/0174323 to Coleman, III et al.; 2011/0247640 to Beeson et al.; 2011/0259353 to Coleman, III et al.; 2012/0037175 to Cantrell et al.; 2012/0055494 to Hunt et al.; 2012/0103353 to Sebastian et al.; 2012/0125354 to Byrd et al.; 2012/0138073 to Cantrell et al.; and 2012/0138074 to Cantrell et al; PCT WO 04/095959 to Arnarp et al.; PCT WO 05/063060 to Atchley et al.; PCT WO 05/004480 to Engstrom; PCT WO 05/016036 to Bjorkholm; PCT WO 05/041699 to Quinter et al., and PCT WO 10/132444 to Atchley; each of which is incorporated herein by reference.

One type of smokeless tobacco product is referred to as "snuff." Representative types of moist snuff products, commonly referred to as "snus," have been manufactured in Europe, particularly in Sweden, by or through companies such as Swedish Match AB, Fiedler & Lundgren AB, Gustavus AB, Skandinavisk Tobakskompagni A/S, and Rocker Production AB. Snus products available in the U.S.A. have been marketed under the tradenames Camel Snus Frost, Camel Snus Original and Camel Snus Spice by R. J. Reynolds Tobacco Company. See also, for example, Bryzgalov et al., 1N1800 Life Cycle Assessment, Comparative Life Cycle Assessment of General Loose and Portion Snus (2005). In addition, certain quality standards associated with snus manufacture have been assembled as a so-called GothiaTek standard. Representative smokeless tobacco products also have been marketed under the tradenames Oliver Twist by House of Oliver Twist A/S; Copenhagen moist tobacco, Copenhagen pouches, Skoal Bandits, Skoal Pouches, SkoalDry, Rooster, Red Seal long cut, Husky, and Revel Mint Tobacco Packs by U.S. Smokeless Tobacco Co.; Marlboro Snus and "taboka" by Philip Morris USA; Levi Garrett, Peachy, Taylor's Pride, Kodiak, Hawken Wintergreen, Grizzly, Dental, Kentucky King, and Mammoth Cave by American Snuff Company, LLC; Camel Snus, Camel Orbs, Camel Sticks, and Camel Strips by R. J. Reynolds Tobacco Company. Other exemplary smokeless tobacco products that have been marketed include those referred to as Kayak moist snuff and Chatanooga Chew chewing tobacco by Swisher International, Inc.; and Redman chewing tobacco by Pinkerton Tobacco Co. LP.

Through the years, various treatment methods and additives have been proposed for altering the overall character or nature of tobacco materials utilized in tobacco products. For example, additives or treatment processes have been utilized in order to alter the chemistry or sensory properties of the tobacco material, or in the case of smokable tobacco materials, to alter the chemistry or sensory properties of mainstream smoke generated by smoking articles including the tobacco material. The sensory attributes of cigarette smoke can be enhanced by incorporating flavoring materials into various components of a cigarette. Exemplary flavoring additives include menthol and products of Maillard reactions, such as pyrazines, aminosugars, and Amadori compounds. American cigarette tobacco blends typically contain a casing composition that includes flavoring ingredients, such as licorice or cocoa powder and a sugar source such as high fructose corn syrup. See also, Leffingwell et al., *Tobacco Flavoring for Smoking Products*, R. J. Reynolds Tobacco Company (1972), which is incorporated herein by reference. In some cases, treatment processes involving the use of heat can impart to the processed tobacco a desired color or visual character, desired sensory properties, or a desired physical nature or texture. Various processes for preparing flavorful and aromatic compositions for use in tobacco compositions are set forth in U.S. Pat. No. 3,424,171 to Rooker; U.S. Pat. No. 3,476,118 to Luttich; U.S. Pat. No. 4,150,677 to Osborne, Jr. et al.; U.S. Pat. No. 4,986,286 to Roberts et al.; U.S. Pat. No. 5,074,319 to White et al.; U.S. Pat. No. 5,099,862 to White et al.; U.S. Pat. No. 5,235,992 to Sensabaugh, Jr.; U.S. Pat. No. 5,301,694 to Raymond et al.; U.S. Pat. No. 6,298,858 to Coleman, III et al.; U.S. Pat. No. 6,325,860 to Coleman, III et al.; U.S. Pat. No. 6,428,624 to Coleman, III et al.; U.S. Pat. No. 6,440,223 to Dube et al.; U.S. Pat. No. 6,499,489 to Coleman, III; and U.S. Pat. No. 6,591,841 to White et al.; US Pat. Appl. Pub. Nos. 2004/0173228 to Coleman, III and 2010/0037903 to Coleman, III et al., each of which is incorporated herein by reference.

The sensory attributes of smokeless tobacco can also be enhanced by incorporation of certain flavoring materials. See, for example, US Pat. Appl. Pub. Nos. 2002/0162562 to Williams; 2002/0162563 to Williams; 2003/0070687 to Atchley et al.; 2004/0020503 to Williams, 2005/0178398 to Breslin et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0029117 to Mua et al.; 2008/0173317 to Robinson et al.; and 2008/0209586 to Neilsen et al., each of which is incorporated herein by reference.

It would be desirable to provide additional compositions and methods for altering the character and nature of tobacco (and tobacco compositions and formulations) useful in the manufacture of smoking articles and/or smokeless tobacco products.

SUMMARY OF THE INVENTION

The present invention provides materials from *Nicotiana* species (e.g., tobacco-derived materials) comprising isolated components from plants of the *Nicotiana* species useful for incorporation into tobacco compositions utilized in a variety of tobacco products, such as smoking articles and smokeless tobacco products. The invention also provides methods for extracting components from *Nicotiana* species (e.g., tobacco materials), and methods for processing those components and tobacco materials incorporating those components.

In particular, the invention provides clarified protein-enriched materials derived from tobacco materials, methods of obtaining and/or deriving such protein-enriched materials, and methods for incorporation of such protein-enriched materials into various tobacco compositions.

In certain aspects, the present disclosure provides a method for obtaining a protein-enriched material from a plant of the *Nicotiana* species or portion thereof, comprising: receiving a plant material of the *Nicotiana* species; contacting the plant material with a solvent for a time and under conditions sufficient to extract one or more proteins from the plant material into the solvent and form a liquid protein-containing extract; separating a solid extracted plant material from the liquid protein-containing extract; clarifying the liquid protein-containing extract to form a clarified protein-containing extract and a solids fraction; and treating the clarified protein-containing extract so as to provide a protein-enriched material comprising at least about 60% protein by dry weight.

The conditions and reagents used in the various steps of the method can vary. For example, the plant material of the *Nicotiana* species treated as described herein can be in the form of a green plant material, yellowed plant material, cured plant material, or a mixture thereof. In certain embodiments, the solvent comprises water and can optionally further comprise sodium metabisulfite, a buffer (e.g., ascorbic acid or glycine), or a combination thereof. In some embodiments, the solvent has a basic pH.

Each step of the method can comprise various components. For example, in some embodiments, the clarifying step comprises adjusting the pH of the liquid protein-containing extract to an acidic pH and filtering the extract. For example, the pH of the clarified protein-containing extract can be adjusted to a pH of between about 4 and about 6, or can be adjusted to a pH of about 5 or about 6. In some embodiments, the clarifying step comprises adjusting the pH of the liquid protein-containing extract to a basic pH and filtering the extract.

In some embodiments, the treating step comprises adjusting the pH of the clarified protein-containing extract to a pH of less than about 6 to form an acidic extract; isolating a precipitate from the acidic extract; and washing the precipitate to provide a protein-enriched material. The pH to which the clarified protein-containing extract is adjusted can, in certain such embodiments, be adjusted to between about 4.5 and about 6 (to provide a RuBisCO-containing protein-enriched material). The washing can be conducted, for example, on a filter having a pore size of between about 1 μm and about 1 kDa or between about 1 μm and about 10 μm. In one embodiment, the extract remaining after the isolating step can be further treated by one or both of: 1) filtration on a filter having a pore size of 1 kDa-500 kDa and isolating a second protein-enriched material as a retentate; and 2) adjusting the extract to a pH of less than about 4.5 and isolating a second precipitate comprising a second protein-enriched material therefrom, wherein the second protein-enriched material is an F2 protein-containing protein-enriched material. In some such embodiments, the pH of the clarified protein-containing extract can be adjusted to a pH of between about 3 to about 4.5 to provide a mixed RuBisCO-containing and F2 protein-containing protein-enriched material.

The solvent used in the washing step can be, for example, an acidic solution (e.g., a citric acid solution). The protein-enriched material produced by this precipitate-forming method generally can, in some embodiments, comprise at least about 80% protein by dry weight. In certain embodiments, the protein thus obtained is at least about 50% RuBisCO by dry weight.

In other embodiments, the treating step comprises filtering the clarified protein-containing extract on a ceramic filter or an ultrafiltration membrane to give a retentate and a liquid permeate; and washing the retentate to provide the protein-enriched material. In certain such embodiments, the clarifying step can comprise adjusting the pH of the liquid protein-containing extract. In some embodiments, the filtering step comprises passing the clarified protein-containing extract through one or more filters having pore sizes and/or molecular weight cutoffs of between about 1 µm and about 1 kDa. In some embodiments, filters having molecular weight cutoffs of about 10 and/or about 20 kDa can be used. For example, the filtering step may comprise passing the clarified protein-containing extract through a filter having a pore size of between about 1 µm and about 500 kDa and wherein the retentate comprises at least about 50% RuBisCO by dry weight. As another example, the filtering step may comprise passing the clarified protein-containing extract through a filter having a molecular weight cutoff of about about 1 kDa or greater, e.g., between about 1 kDa and about 500 kDa and the retentate may comprise a mixture of RuBisCO and F2 protein. In some such embodiments, the method can further comprise passing the 1 kDa permeate through a filter having a pore size of between about 500 kDa and 1 kDa to give a second protein-enriched material retentate comprising F2 fraction proteins.

In some embodiments, the method can further comprise spray drying, freeze drying, or otherwise dehydrating the solid, protein-enriched material. Additionally, various components can optionally be added to remove color, odor, taste, alkaloids, metals, or a combination thereof at any step of the process. Such components can be, for example, selected from the group consisting of activated carbon, a resin, clay, a chelating agent, a molecularly imprinted polymer, a non-imprinted polymer, or a combination thereof.

In another aspect of the present disclosure is provided a protein-enriched extract obtained according to the methods described herein. In another aspect is provided a product comprising a protein-enriched extract as described herein. For example, such products can include, but are not limited to, dietary supplements, foods, beverages, personal care items, pharmaceutical products, and pet food.

In a further aspect is provided a protein-enriched material derived from a plant of the *Nicotiana* species or a portion thereof, wherein the material comprises at least about 60% protein by dry weight. The makeup of the protein-enriched material can vary and may, for example, comprise RuBisCO, F2 proteins, or a combination thereof. In certain embodiments, the protein in the protein-enriched material comprises at least about 50%, at least about 60%, at least about 70%, at least about 80%, or at least about 90% RuBisCO by weight. In certain embodiments, the protein in the protein-enriched material comprises at least about 50%, at least about 60%, at least about 70%, at least about 80%, or at least about 90% F2 proteins by weight.

BRIEF DESCRIPTION OF THE DRAWINGS

In order to provide an understanding of embodiments of the invention, reference is made to the appended drawings, which are not necessarily drawn to scale, and in which reference numerals refer to components of exemplary embodiments of the invention. The drawings are exemplary only, and should not be construed as limiting the invention.

DETAILED DESCRIPTION OF THE PREFERRED EMBODIMENTS

Figure 1:
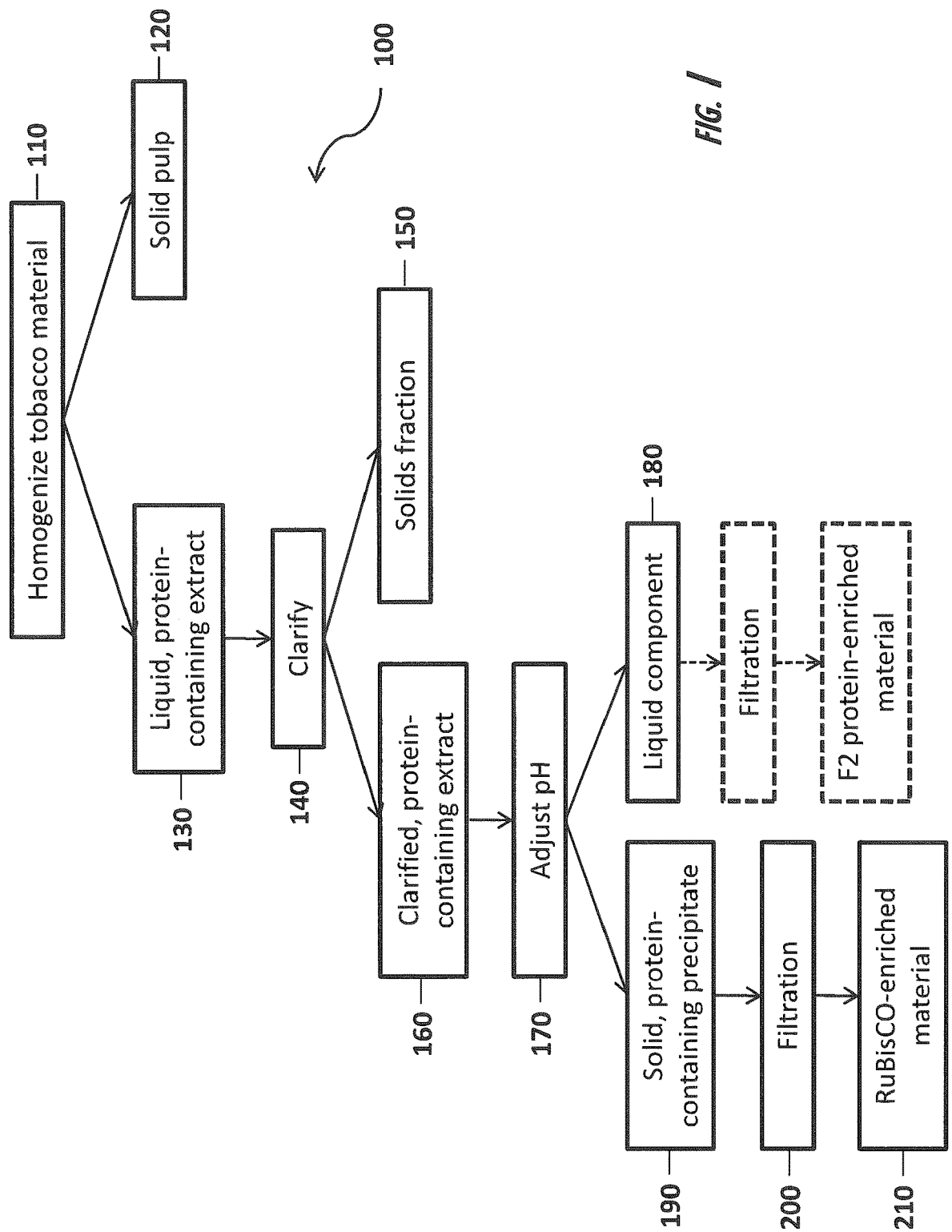
FIG. 1 is a schematic of one process embodiment for the derivation of protein from a tobacco material.

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water).

The present disclosure provides processes for isolating, separating, or otherwise extracting protein from a biomass such as a plant material (e.g., tobacco). Although the present disclosure focuses primarily on extraction of protein from tobacco, it is noted that the methods may be generally applicable to plant materials other than tobacco. In some embodiments, the processes can be tailored to extraction of one or more specific protein types or may be generalized to extraction of proteins based on solubilities, compound type, compound chemical properties, compound physical properties, or the like. Generally, the water-soluble portion of plant biomass consists of two fractions. One fraction predominantly comprises RuBisCO, whose subunit molecular weight is about 550 kD (commonly referred to as a "Fraction 1 protein" or "F1 protein"). RuBisCO may comprise up to about 25% of the total protein content of a leaf and up to about 10% of the solid matter of a leaf. A second fraction ("Fraction 2 protein" or "F2 protein") generally contains a mixture of proteins and peptides with molecular weights ranging from about 3 kD to about 100 kD and may also contain other compounds including sugars, vitamins, alkaloids, flavors, and amino acids.

One exemplary protein for extraction according to process described herein is ribulose-1,5-bisphosphate carboxylase oxygenase (commonly referred to as RuBisCO). RuBisCO is largely considered to be the most abundant protein in the world, as it is present in every plant that undergoes photosynthesis. RuBisCO is essential to the initial step of the photosynthetic fixation of carbon dioxide and functions to catalyze the carboxylation and/or oxygenation of ribulose-1,5-bisphosphate. For many applications (e.g., food products, feed products, and industrial products), it may be desirable to replace certain animal proteins with plant proteins. Additionally, in some applications, it may be desirable to replace certain other plant proteins (e.g., soy proteins and/or genetically modified proteins). RuBisCO has been found to exhibit good nutritional properties and is colorless, tasteless, and odorless. Further, certain physical properties of RuBisCO render it advantageous for use in such products, as it has excellent binding, gelling, solubility, and emulsifying behavior.

Various methods have been proposed for the extraction of RuBisCO from a wide array of plant materials. For example, see U.S. Pat. No. 4,268,632 to Wildman et al., U.S. Pat. No. 4,340,676 to Bourke; U.S. Pat. No. 4,400,471 to Johal; U.S. Pat. No. 4,588,691 to Johal; and U.S. Pat. No. 6,033,895 to Garger et al., which are incorporated herein by reference. However, a process for the extraction and purification of RuBisCO on a large (industrial) scale has not yet been demonstrated.

The present disclosure provides a method for the extraction and/or isolation of certain proteins from a plant of the Nicotiana species or a portion thereof. Accordingly, the methods disclosed herein may, in some embodiments, provide a protein-enriched material, e.g., a material comprising at least about 50% protein by dry weight, at least about 60% protein by dry weight, at least about 70% protein by dry weight, at least about 80% protein by dry weight, or at least about 85% protein by dry weight. In some embodiments, the protein-enriched material comprises a mixture of RuBisCO and F2 proteins. In some embodiments, the protein in the protein-enriched material comprises primarily RuBisCO. In some embodiments, the protein in the protein-enriched material comprises primarily F2 proteins.

In some embodiments, the protein comprises at least about 60% RuBisCO by dry weight, at least about 70% RuBisCO by dry weight, or at least about 80% RuBisCO by dry weight, at least about 90% RuBisCO by dry weight, at least about 95% RuBisCO by dry weight, at least about 98% RuBisCO by dry weight, or at least about 99% RuBisCO by dry weight. It is noted that where the term "protein-enriched" is used herein, this may in some embodiments, refer to "RuBisCO-enriched," as described below.

In some embodiments, the present disclosure specifically provides a method for the extraction and/or isolation of RuBisCO from a plant of the Nicotiana species or a portion thereof. Accordingly, the methods disclosed herein may, in some embodiments, provide a RuBisCO-enriched material, e.g., a material comprising at least about 50% RuBisCO by dry weight, at least about 60% RuBisCO by dry weight, at least about 70% RuBisCO by dry weight, at least about 80% RuBisCO by dry weight, or at least about 85% RuBisCO by dry weight.

In certain embodiments, the present disclosure further provides a method for the extraction and/or isolation of F2 proteins from a plant of the Nicotiana species or a portion thereof. Accordingly, the methods disclosed herein may, in some embodiments, provide an F2 protein-enriched material, e.g., a material comprising at least about 10% F2 protein by weight, at least about 20% F2 protein by weight, at least about 30% F2 protein by weight, at least about 40% F2 protein by weight, at least about 50% F2 protein by weight, or at least about 60% F2 protein by weight.

The present disclosure is applicable, in some embodiments, for large scale production, where the term large scale production refers to processing large quantities of a biomass (e.g., tobacco) on a mass production level. The term "biomass" and related terms such as "biomatter" and "plant source" are understood to refer to any portion of a harvested plant that may be processed to extract, separate, or isolate components of interest therefrom. The processing may be carried out in relation to various plants or portions thereof, such as seeds, flowers, stalks, stems, roots, tubers, leaves, or any further portions of the plant.

Exemplary tobacco plant materials used in accordance with the present disclosure may be of some form of a plant of the Nicotiana species. The selection of the plant from the Nicotiana species can vary; and in particular, the types of tobacco or tobaccos may vary. Tobaccos that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Passanda, Cubano, Jatin and Bezuki tobaccos), light air cured (e.g., North Wisconsin and Galpao tobaccos), Indian air cured, Red Russian and Rustica tobaccos, as well as various other rare or specialty tobaccos. Descriptions of various types of tobaccos, growing practices and harvesting practices are set forth in *Tobacco Production, Chemistry and Technology*, Davis et al. (Eds.) (1999), which is incorporated herein by reference. Nicotiana species can be derived using genetic-modification or crossbreeding techniques (e.g., tobacco plants can be genetically engineered or crossbred to increase or decrease production of or to other change certain components, characteristics or attributes). Additional information on types of Nicotiana species suitable for use in the present invention can be found in US Pat. Appl. Pub. No. 2012/0192880 to Dube et al., which is incorporated by reference herein. Tobacco plants can be grown in greenhouses, growth chambers, or outdoors in fields, or grown hydroponically.

The Nicotiana species can be selected for the content of various compounds that are present therein. For example, plants can be selected on the basis that those plants produce relatively high quantities of one or more of the compounds desired to be isolated therefrom (e.g., proteins). In certain embodiments, plants of the Nicotiana species (e.g., Galpao commun tobacco) are specifically grown for their abundance of leaf surface compounds.

The portion or portions of the plant of the Nicotiana species used according to the present invention can vary. For example, virtually all of the plant (e.g., the whole plant) can be harvested, and employed as such. Alternatively, various parts or pieces of the plant can be harvested or separated for further use after harvest. For example, the leaves, stem, stalk, roots, lamina, flowers, seed, and various portions and combinations thereof, can be isolated for further use or treatment. The plant material of the invention may thus comprise an entire plant or any portion of a plant of the Nicotiana species. See, for example, the portions of tobacco plants set forth in US Pat. Appl. Pub. Nos. 2011/0174323 to Coleman, III et al. and 2012/0192880 to Dube et al., which are incorporated by reference herein.

The plant of the Nicotiana species can be employed in either an immature or mature form, and can be used in either a green form or a cured form, as described in 2012/0192880 to Dube et al., which is incorporated by reference herein.

The tobacco material can be subjected to various treatment processes such as, refrigeration, freezing, drying (e.g., freeze-drying or spray-drying), irradiation, yellowing, heating, cooking (e.g., roasting, frying or boiling), fermentation, bleaching or otherwise subjected to storage or treatment for later use. In some embodiments, harvested tobacco can be sprayed with a buffer or antioxidant (e.g., a sodium metabisulfite buffer) to prevent the green plants from browning prior to further treatment as described herein. Other exemplary processing techniques are described, for example, in US Pat. Appl. Pub. Nos. 2009/0025739 to Brinkley et al. and 2011/0174323 to Coleman, III et al., which are incorporated by reference herein. At least a portion of the plant of the Nicotiana species can be treated with enzymes and/or probiotics before or after harvest, as discussed in U.S. patent application Ser. No. 13/444,272 to Marshall et al., filed on Apr. 11, 2012 and U.S. patent application Ser. No. 13/553,222 to Moldoveanu, filed on Jul. 19, 2012, which are incorporated herein by reference.

A harvested portion or portions of the plant of the *Nicotiana* species can be physically processed. A portion or portions of the plant can be separated into individual parts or pieces (e.g., roots can be removed from stalks, stems can be removed from stalks, leaves can be removed from stalks and/or stems, petals can be removed from the remaining portion of the flower). Although any single part of the tobacco plant or multiple parts of the tobacco plant can be used according to the present invention, preferably tobacco stalk, tobacco leaves, or both tobacco stalk and leaves are used. The harvested portion or portions of the plant can be further subdivided into parts or pieces (e.g., shredded, cut, comminuted, pulverized, milled or ground into pieces or parts that can be characterized as filler-type pieces, granules, particulates or fine powders). The harvested portion or portions of the plant can be subjected to external forces or pressure (e.g., by being pressed or subjected to roll treatment). For example, in certain embodiments, tobacco stalk, either alone or in combination with other portions of the plant (e.g., stalk and leaf together) can be used and may, in some embodiments, be subjected to the types of treatment described in US Pat. Appl. Publ. No. 2012/0152265 to Dube et al., which is incorporated herein by reference.

When carrying out such processing conditions, the harvested portion or portions of the plant can have a moisture content that approximates its natural moisture content (e.g., its moisture content immediately upon harvest), a moisture content achieved by adding moisture to the harvested portion or portions of the plant, or a moisture content that results from the drying of the harvested portion or portions of the plant. As such, harvested portion or portions of the plant can be used as such as components of tobacco products, or processed further.

According to the present invention, a portion or portions of a plant of the *Nicotiana* species are treated so as to provide one or more components (e.g., proteins) contained therein in a more usable (e.g., more concentrated) form. Various compounds or mixtures of compounds from the *Nicotiana* plant or portions thereof can be extracted and/or isolated by the methods provided herein. As used herein, an "isolated component," or "plant isolate," is a compound or complex mixture of compounds separated from a plant of the *Nicotiana* species or a portion thereof. The isolated component can be a single compound, a homologous mixture of similar compounds (e.g., isomers of a compound), or a heterologous mixture of dissimilar compounds (e.g., a complex mixture of various compounds of different types). See, for example, the description of isolated tobacco components and techniques for isolation in US Pat. Appl. Pub. Nos. 2007/0137663 to Taylor et al.; 2011/0174323 to Coleman, III et al.; 2011/0259353 to Coleman, III et al.; 2012/0141648 to Morton et al.; 2012/0192880 to Dube et al.; 2012/0192882 to Dube et al.; 2012/0272976 to Byrd et al., 2012/0211016 to Byrd, Jr. et al., and U.S. patent application Ser. No. 13/647,670 to Gerardi et al., which are incorporated by reference herein.

An illustration of an exemplary set of processing steps that can be carried out to obtain a RuBisCO-enriched extract from a tobacco plant or portion thereof according to one embodiment of the invention is presented in FIG. 1. The specific sequence of steps illustrated in FIG. 1 should not be construed as limiting of the invention. Any modifications to the present disclosure which are functionally equivalent to the procedures and conditions disclosed herein are within the scope of the instant invention. For example, typical separation processes can include one or more process steps such as solvent extraction (e.g., using polar solvents, organic solvents, or supercritical fluids), chromatography (e.g., preparative liquid chromatography), clarification, distillation, filtration (e.g., ultrafiltration), recrystallization, and/or solvent-solvent partitioning. In some embodiments, the tobacco plant or portion thereof can be pre-treated, e.g., to liberate certain compounds to make the desired compounds available for more efficient separation. In some embodiments, multiple methods are used to obtain the desired compounds.

The process illustrated in FIG. 1 can be viewed in some embodiments as comprising a group of processes 100 that individually can be carried out to obtain certain proteins from tobacco plants or portions thereof. In certain embodiments, the processes used according to the present invention can be viewed as a holistic plant component isolation and extraction process because the individual process steps provide for isolation or extraction of specifically desired plant components in a manner that does not preclude isolation or extraction of any other plant component in the same batch. For exemplary details on the specific types of processing that can be conducted, see US Pat. App. Publ. No. 2012/0141648 to Morton et al., which is incorporated herein by reference.

As shown in the embodiment illustrated in FIG. 1, a tobacco material can be homogenized (110) to provide a solid pulp 120 and a liquid, protein-containing extract 130. Extract 130 is clarified (140) to remove solids therefrom, giving a solids fraction 150 and a clarified, protein-containing extract 160. Extract 160 is pH-adjusted (170) and separated into a liquid component 180 and a solid, protein-containing precipitate 190. Precipitate 190 is subjected to filtration to give a RuBisCO-enriched material 210. Optionally, liquid component 180 can be treated to give an F2 protein-enriched material.

The homogenizing step 110 involves any type of processing of a plant material that is effective to break down the plant material and release component parts thereof. Specifically, homogenizing can refer to any processing that is effective to disrupt or break apart plant cell walls and release fluid and other materials contained within the plant cells. Such processing can include the use of an apparatus, such as a grinder, extruder, hammer mill, colloid mill, French press, or the like, as described in more detail in US Pat. Appl. Publ. 2012/0141648 to Morton et al., which is incorporated herein by reference. Homogenizing step 110 may be performed, in some embodiments, in the presence of an extraction solvent. In this regard, the plant material may be subjected to a combined grinding and extraction process that subjects the plant material to a grinding action and simultaneously contacts the plant material with the extraction solvent. Alternatively, the homogenizing step may be conducted and subsequently, the ground material can be contacted with the extraction solvent. Thus, the plant material may be combined with the extraction solvent prior to, during, or after grinding.

Exemplary techniques useful for extracting components from *Nicotiana* species are described or referenced in US Pat. Appl. Pub. Nos. 2011/0259353 to Coleman, III et al. and 2012/0211016 to Byrd, Jr. et al., which are incorporated by reference herein. The extraction solvent for the extraction of proteins from tobacco according to the methods provided herein is preferably water (i.e., an aqueous solvent). Other exemplary extraction and separation solvents or carriers include alcohols (e.g., methanol or ethanol), hydrocarbons (e.g., heptane and hexane), diethyl ether, methylene chloride, supercritical carbon dioxide, and combinations thereof.

In some embodiments, the solvent may include any one or more of a variety of compounds useful to facilitate extraction of one or more specific components from the plant material. For example, in some embodiments, the extraction solvent may comprise one or more materials selected from the group consisting of co-solvents, detergents, surfactants, antioxidants, amino acids, buffers, protein extraction agents, enzymes, mineral acids, and combinations thereof. In some embodiments, the extraction solvent may comprise: glycine, one or more salts of phosphoric acid (e.g., as buffer materials), one or more Group I or Group II halide salts (including NaCl, e.g., as protein extraction agents), and/or an antioxidant/reducing agent (e.g., sodium metabisulfite ($Na_2S_2O_5$), sodium bisulfate, or ascorbic acid).

In some embodiments, the extraction solvent may comprise a buffer solution that can be particularly useful to maintain or otherwise adjust the pH of the plant liquid component during the homogenizing step to a predetermined constant level. Advantageously, one or more antioxidants and/or buffers (e.g., sodium metabisulfate, ascorbic acid, and/or glycine) are included in the extraction solvent, e.g., to suppress undesirable oxidation. When the extraction solvent functions as a buffer solution, it can be useful for the extraction solvent to include one or more neutralizing agents such as, for example, sodium phosphate. Because of the intimate mixing occurring during homogenization in the presence of the extraction solvent, it is understood that the liquid, protein-containing extract 130 can comprise not only the liquid components from the plant material but also some amount of the extraction solvent.

According to some embodiments, the pH of the extraction solvent may be adjusted so as to maximize the amount of a specific plant component (e.g., protein) in the liquid, protein-containing extract thus provided. For example, it may be useful to maintain the pH within a basic range or within an acidic range. For example, in some embodiments, the pH of the extraction solvent can be basic, e.g., within the range of about 7-14, e.g., about 8-12, such as about 9-11 (e.g., about 10.5). Such a range specifically can be useful in relation to embodiments wherein it is desirable to maximize the protein content of the liquid, protein-containing extract.

The extraction solvent preferably can be combined with the plant material in specific ratios to achieve extraction of the desired components. In some embodiments, the extraction solvent and the plant material may be combined at a ratio of about 0.1 L to about 5 L of extraction solvent per 1 kg of biomass. In other embodiments, the ratio may be about 0.1 L to about 4 L, about 0.1 to about 3 L, about 0.1 to about 2 L, about 0.1 to about 1 L, about 0.2 L to about 0.8 L, about 0.3 L to about 0.7 L, or about 0.4 L to about 0.6 L of extraction solvent per 1 kg of biomass. In further embodiments, the process may use at least about 0.1 L, at least about 0.2 L, at least about 0.3 L, or at least about 0.4 L of extraction solvent per 1 kg of biomass. In one embodiment, the process can comprise combining about 0.5 L of extraction solvent per 1 kg or biomass.

The conditions of the extraction process can vary. In some embodiments, the plant of the *Nicotiana* species is combined with a solvent to form a material (e.g., in the form of a suspension or slurry). In certain embodiments, the amount of solvent added to form the moist material can be at least about 50 weight percent, or at least about 60 weight percent, or at least about 70 weight percent, based on the total weight of the material. In some cases, the amount of solvent can be described as at least about 80 weight percent or at least about 90 weight percent.

Advantageously, the extraction is done in the absence of heating. However, the tobacco material in homogenizing step 110 can, in some embodiments, be heated at various temperatures and pressures. In certain embodiments, the material is heated to elevated temperatures (e.g., above room temperature) to effect extraction of compounds in the particulate material. For example, the moist material can be heated to greater than about 50° C., greater than about 60° C., greater than about 70° C., greater than about 80° C., greater than about 90° C., greater than about 100° C., greater than about 125° C., greater than about 150° C., greater than about 175° C., or greater than about 200° C. In certain embodiments, the pressure and temperature are adjusted such that the temperature of the moist material is elevated compared to the boiling point of water (or other solvent) at atmospheric pressure. One of skill in the art will be aware that the boiling point of a liquid is related to its pressure, and therefore will be able to adjust the pressure and temperature accordingly to cause boiling of the material.

The heating can be conducted in a pressure-controlled and pressurized environment, although atmospheric pressure in a vented tank can be used without departing from the invention. Preferred pressure vessels are equipped with an external heating source, and can also be equipped with means for agitation, such as an impeller. In other embodiments, the heat treatment process is conducted using an enclosed container placed in a microwave oven, a convection oven, or heated by infrared heating. Examples of vessels that provide a pressure-controlled environment are set forth in US Pat. Appl. Pub. No. 2012/0192880 to Dube et al., which is incorporated by reference herein. Typical pressures experienced by the reaction mixture during the heating process often range from about 10 psig to about 1,000 psig, normally from about 20 psig to about 500 psig.

The heating can be conducted in atmospheric air, or ambient atmosphere or within a controlled atmosphere, such as a generally inert atmosphere. Gases such as nitrogen, argon and carbon dioxide can be used. Alternatively, a hydrocarbon gas (e.g., methane, ethane or butane) or a fluorocarbon gas also can provide at least a portion of a controlled atmosphere in certain embodiments, depending on the choice of treatment conditions and desired reaction products.

The amount of time required to effectuate extraction is partially dependent on the temperature and pressure at which the extraction is conducted. For example, in some embodiments, heating the material to an elevated temperature and/or pressurizing the material increases the rate of extraction. The time range for the extraction process is typically at least about 30 minutes (e.g., at least about 1 hour or at least about 2 hours) and typically less than about 24 hours (e.g., less than about 12 hours or less than about 8 hours), although other time periods could be used without departing from the invention. In some embodiments, multiple extractions can be conducted to extract additional compounds therefrom. See, for example, US Patent App. Publ. No. 2008/0254149 to Havkin-Frenkel, which is incorporated herein by reference.

After the tobacco material is homogenized, the resulting material can be separated into a solid pulp 120 and a liquid, protein-containing extract 130 (i.e., the liquid extracted from the processed plant material according to the present disclosure). The separating can be done by any means, e.g., a rough filtration or other method for withdrawal of the liquid component from the homogenized mixture. The solid pulp 120 generally contains primarily plant fiber (or cellulose) and pectin and can, in some embodiments, be separately processed as provided in US Pat. Appl. Pub. 2012/0141648 to Morton et al., which is incorporated herein by reference.

The liquid, protein-containing extract 130 can, in various embodiments, be in the form of a green or brown juice; however, it should be understood that the term "liquid, protein-containing extract" may refer to any liquid extracted from a plant material or biomatter, regardless of the extracted liquid's color. Extract 130 may, in some embodiments, comprise components including, but not limited to, proteins, peptides, sugars, and/or alkaloids. The liquid, protein-containing extract typically comprises some level of solid (insoluble) material entrained in the liquid. The extract may be characterized as being a slurry, suspension, or solution, depending upon the specific embodiment, which can be determined based upon the type of plant material used, the specific extraction solvent used, and the component desired for isolation.

Following homogenization and separation from solid pulp 120, the protein-containing extract 130 can be processed to clarify the juice as illustrated by step 140 of FIG. 1. Clarification generally results in the removal of some or all of the portion of the plant material that is insoluble in the extraction solvent of the protein-containing extract. In some embodiments, clarification can result in the removal of additional high-molecular weight components of extract 130. The clarification step provides a solids fraction 150 and a clarified, protein-containing extract 160. Clarification can be an important step in achieving a desired concentration of certain desired plant components (e.g., protein) in the soluble fraction. See, for example, the clarification techniques set forth in US Patent App. Publ. No. 2012/0152265 to Dube et al., which is incorporated by reference herein.

In certain embodiments, clarification comprises multiple steps, including, but not limited to, one or more chemical treatment steps, one or more heating steps, one or more filtration steps, one or more other types of separation steps (e.g., centrifugation and/or sedimentation), or some combination thereof. Where clarification comprises multiple steps, it is to be understood that these multiple steps can be conducted in any order.

Clarification step 140 can, in some embodiments, involve the addition of various materials (i.e., clarifying agents) to an extracted liquid. For example, specific clarifying agents that may be added to the raw, extracted liquid include, but are not limited to, various salts, lime, sulfur, and other compounds to stabilize or clarify the liquid. In certain embodiments, the pH of the extract can be modified, e.g., via the addition of a suitable amount of an acid or base. Exemplary acidic or basic materials useful for this purpose include, but are not limited to, citric acid, hydrochloric acid, phosphoric acid, and/or sodium hydroxide. In some embodiments, adjusting the pH of the extract can stabilize or clarify the liquid. In some embodiments, adjusting the pH of the extract can facilitate precipitation of specific components (desirable or undesirable) therefrom, which can subsequently be removed. In certain embodiments, the pH is adjusted such that the extract is slightly acidic (e.g., having a pH between about 5 and about 7). In other embodiments, the pH is adjusted such that the extract is basic (e.g., having a pH between about 7 and about 12).

In some embodiments, added clarifying agents can function as flocculants, which can facilitate the removal of one or more impurities. For example, flocculants and/or filter aids may remove suspended particles and/or dissolved molecules or ions. Some common exemplary filter aids include cellulose fibers, perlite, bentonite, diatomaceous earth, and other silaceous materials. The flocculants and/or filter aids can subsequently be removed from the liquid by any means (e.g., filtration, settling, centrifugation, etc.). In certain embodiments, activated carbon is added to the extract to remove color, odor, and/or taste therefrom. In place of, or in addition to the activated carbon, various other types of materials can be used to remove color, odor, and/or taste and are intended to be encompassed within the methods described herein.

Advantageously, clarification according to the present disclosure is conducted without increasing the temperature of the protein-containing extract above ambient temperature (i.e., without heating). However, in certain embodiments, clarification step 140 can comprise heating the extract. In some embodiments, the liquid can, be heated to initiate the desired reactions for clarification and/or to solubilize or unsolubilize certain components of the extract. The temperature and time for which the extract is heated can vary. In some embodiments, extract 130 is heated to boiling, which may result in the formation of additional solids, which can subsequently be removed by any of the methods described herein. In some embodiments, it may be desirable to heat the extract to remove some of the solvent (i.e., to concentrate the extract). For example, in one embodiment, the extracted liquid can be heated in a vented vessel to evaporate a portion of the water. The temperature and pressure at which the liquid is heated may vary. See, for example, the solvent removal techniques set forth in US Pat. Pub. No. 2012/0152265 to Dube et al., which is incorporated by reference herein.

In some embodiments, clarifying step 140 comprises introducing the protein-containing extract 130 into a separating apparatus, such as a decanter or a centrifuge (e.g., a decanter centrifuge). In some embodiments, clarifying step 140 comprises passing the extract through a filter press. The extract can thus be processed to separate the extract into a soluble liquid fraction (permeate) (i.e., clarified, protein-containing extract 160) and a solids fraction 150. Representative centrifuge systems are described in, for example, U.S. Pat. No. 6,817,970 to Berit et al., U.S. Pat. No. 5,899,845 to Kohlstette et al., U.S. Pat. No. 5,267,937 to Zettier et al., U.S. Pat. No. 4,966,576 to Schulz et al., and U.S. Pat. No. 5,865,719 to Droste et al., each of which is incorporated herein by reference in its entirety. Suitable conditions for centrifugation may be based, for example, upon time interval, feed rate, dwell time for expulsion of solid pellet material, operation speed, and G-force. Representative filter presses are described, for example, in U.S. Pat. No. 2,843,267 to Anderson; U.S. Pat. No. 3,204,769 to Davis; U.S. Pat. No. 4,354,934 to Kohonen; U.S. Pat. No. 4,512,889 to Noda et al.; U.S. Pat. No. 4,544,448 to Lintunen; and U.S. Pat. No. 5,482,623 to Pierson, which are incorporated herein by reference.

In the embodiment illustrated in FIG. 1, following clarification, the pH of the clarified protein-containing extract 160 is adjusted (step 170 of FIG. 1). The pH of the liquid concentrate may be adjusted by addition of a suitable amount of an acidic or basic material, such as citric acid, hydrochloric acid, phosphoric acid, or sodium hydroxide. In certain embodiments, the pH of extract 160 is adjusted to ensure that the extract is acidic (i.e., having a pH below 7) or basic (i.e., having a pH above 7). In some embodiments, acidifying the extract is preferable to give an extract having a pH within the range of about 4 to about 7, e.g., about 4.5 to about 6.5, or about 5 to about 6, e.g., having a pH of about 5. In certain embodiments, adjusting the pH to about 6 results in a clarified extract. In certain embodiments, adjusting the pH to about 5 results in precipitation of RuBisCO, which can be isolated (e.g., by filtration or decanting the remaining liquid) and subsequently washed. In certain embodiments, it is advantageous to maintain the pH above about 4 or above about 4.5, as a pH below these values may result in precipitation of additional solids in addition to RuBisCO (e.g., other proteins, sugars, and/or starches, etc.).

In other embodiments, however, it may be desirable to precipitate additional proteins (e.g., the F2 fraction proteins). In such embodiments, the pH is adjusted, e.g., to less than about 4.5 (e.g., between about 3 and about 4.5, e.g., about 4). As the pH adjustment step 170 generally results in the precipitation of one or more components of the clarified extract, it may be advantageous to maintain the pH-adjusted extract for a time and temperature sufficient to provide for adequate precipitation and/or settling of the solids.

Following the precipitation and/or settling of the solids, the liquid and solid components are separated to give a liquid component 180 and a solid, protein-containing precipitate 190. The separation of the solid and liquid components can be accomplished in various ways, e.g., by decanting the liquid and/or filtering the mixture. In certain embodiments, the precipitate 190 is white in color. In some embodiments, the precipitate 190 is washed after separation from liquid component 180, e.g., with a citric acid solution. The concentration of the citric acid solution can vary, and is, for example, around 5 mM in certain embodiments. Various solutions can be used in addition to or in place of the citric acid, and advantageously, such solutions comprise only food-grade components. Other exemplary solutions that can be used for this washing step include, but are not limited to, ascorbic acid and/or acetic acid.

Precipitate 190 generally comprises RuBisCO as well as various additional components. It is noted that the content of precipitate 190 may depend, in part, on the pH used in the previous step. For example, where the pH was between about 4.5 and about 6, the precipitate 190 may comprise more RuBisCO, whereas where the pH was less than about 4.5, the precipitate 190 may additionally include a significant amount of, e.g., F2 proteins.

The precipitate 190 can be subjected to one or more filtration steps 200 to isolate RuBisCO from any remaining components (e.g., other proteins, fats, and lipids). The process of filtration can comprise dissolving precipitate 190 (e.g., in an aqueous citric acid solution), passing the liquid through one or more filter screens and/or membranes to remove selected sizes of particulate matter (giving a retentate that remains on or in the filter material and a permeate that passes through the filter material) and/or components of the liquid having a molecular weight above a certain threshold. As RuBisCO is generally the largest component in precipitate 190, a filter or filter membrane is advantageously used which can retain the RuBisCO while allowing the remaining components to pass through. In certain embodiments, a ceramic filter can be used to isolate the RuBisCO.

In some embodiments, microfiltration is employed, wherein the dissolved precipitate 190 is brought into contact with a semipermeable membrane. The membrane can be of any type, such as plate-and-frame (having a stack of membranes and support plates), spiral-wound (having consecutive layers of membrane and support material rolled up around a tube), tubular (having a membrane-defined core through which the feed flows and an outer, tubular housing where permeate is collected), or hollow fiber (having several small diameter tubes or fibers wherein the permeate is collected in the cartridge area surrounding the fibers). The membrane can be constructed of any material. For example, polysulfone, polyethersulfone, polypropylene, polyvinylidenefluoride, and cellulose acetate membranes are commonly used, although other materials can be used without departing from the invention described herein. See, for example, the ultrafiltration techniques (which can be applied to microfiltration as well) as set forth in US Patent App. Publ. No. 2012/0152265 to Dube et al., which is incorporated by reference herein.

Microfiltration membranes are available in a wide range of pore sizes (typically ranging from about 0.05 or 0.1 to about 10 microns). In practice, compounds with molecular weights above the pore size are retained in the retentate, and the compounds with molecular weights below the pore size pass through the filter into the permeate. Microfiltration methods typically are not capable of removing low molecular weight organic compounds and ions.

Microfiltration is typically a cross-flow separation process. The liquid stream to be treated (feed) flows tangentially along the membrane surface, separating into one stream that passes through the membrane (permeate) and another that does not (retentate or concentrate). The operating parameters of the microfiltration system can be varied to achieve the desired result. For example, the feed mixture to be filtered can be brought into contact with the membrane by way of applied pressure. The rate of permeation across the membrane is directly proportional to the applied pressure; however, the maximum pressure may be limited. The flow velocity of the mixture across the membrane surface can be adjusted. Temperature can also be varied. Typically, permeation rates increase with increasing temperature.

Commercial microfiltration system are readily available and may be used for the microfiltration methods of the present invention. For example, commercial suppliers such as Millipore, Spectrum® Labs, Applied Membranes Inc., Pall Corporation, Whatman®, and Porex Corporation manufacture various filter membranes and cartridges, and/or filtration systems (e.g., tangential flow filtration systems). Exemplary membranes include, but are not limited to, Memtek® Microfiltration Systems and Forty-X™ disc filters (from Siemens), MFK Series, Winefilter™ Series, and Super-Cor™ MF Series membranes (from Koch Membrane Systems), Durapore membranes and Pellicon® XL cassettes (from Millipore), Microkros®, Minikros®, and KrosFlo® Hollow Fiber Modules (from Spectrum® Labs), Cyclopore membranes (from Whatman®) Scepter® Membranes (Graver Technologies), and Torayfil® microfiltration membranes (from Toray Industries, Inc.). In certain embodiments, the membranes are ceramic membranes, including, but not limited to, Membralox® membranes (from Pall Corporation), MF membranes (from CleaNSep Systems), ceramic membranes (from Sterlitech Corporation), Inside-CeRAM™ membranes, Filtanium™ membranes, and Isoflux™ membranes (from Tami Industries), and CeraMem® Ceramic Membranes (from Veolia Water). Commercially available filtration systems include, but are not limited to, Millipore's Labscale™ Tangential Flow Filtration (TFF) system and Spectrum® Labs' KrosFlo® and MiniKros® Tangential Flow Filtration Systems.

In certain embodiments, a multistage filtration process can be used. Such embodiments employ multiple filters and/or membranes of different (typically decreasing) molecular weight cutoffs. Any number of filters and/or membranes can be used in succession according to the invention. Further filtration means suitable for use in the various embodiments of the invention where filtration is desirable include those disclosed in U.S. Pat. No. 4,941,484 to Clapp et al., the disclosure of which is incorporated herein by reference in its entirety. In some cases, the microfiltration step in this embodiment can be replaced with, or combined with, one or more ultrafiltration steps described herein.

The filter or series of filters (e.g., a single, 1.4 μm ceramic filter) advantageously retains a solid, RuBisCO-enriched material 210 as the retentate and preferably allows a majority of the additional components of precipitate 190 to pass through the filter into the permeate. The retentate is then washed (e.g., with 5 mM citric acid) to yield a RuBisCO-enriched material 210. As noted above, various solutions (e.g., solutions comprising food-grade components such as acetic acid and/or ascorbic acid) can be used in addition to or instead of citric acid. The RuBisCO-enriched extract provided according to the method of FIG. 1, in some embodiments, comprises at least about 60% RuBisCO by dry weight, at least about 70% RuBisCO by dry weight, at least about 80% RuBisCO by dry weight, at least about 90% RuBisCO by dry weight, at least about 95% RuBisCO by dry weight, at least about 98% RuBisCO by dry weight, or at least about 99% RuBisCO by dry weight. The RuBisCO-enriched extract can be provided in various forms, including, e.g., a semi-solid form or solid form. The extract can, in some embodiments, be dehydrated to produce a true solid form. Advantageously, the method of FIG. 1 is applicable at an industrial scale. While various processes have been previously reported for the isolation of RuBisCO from various plants, none of these has been shown to be applicable at such a large scale. Advantageously, the process described herein relies principally on the use of ceramic filtration to provide the desired product, a method which is readily scalable. In contrast, traditional methods commonly employ one or more centrifugation steps, which are difficult to translate to an industrial scale.

As shown in FIG. 1, the liquid component 180 can optionally be treated to produce a F2 protein-enriched material. As noted, by appropriate pH selection, protein-containing precipitate 190 can, in some embodiments, comprise primarily RuBisCO. In such embodiments, a significant amount of F2 fraction is typically contained in the liquid component. That liquid component can be treated, for example, by filtration (e.g., through a filter or membrane on which the F2 proteins are generally retained, while allowing certain remaining components to pass through) or by precipitation (e.g., by adjusting the pH of the liquid component 180 to a pH sufficient to precipitate the F2 proteins, such as less than about 4.5, preferably between about 3 and about 4.5).

Figure 2:
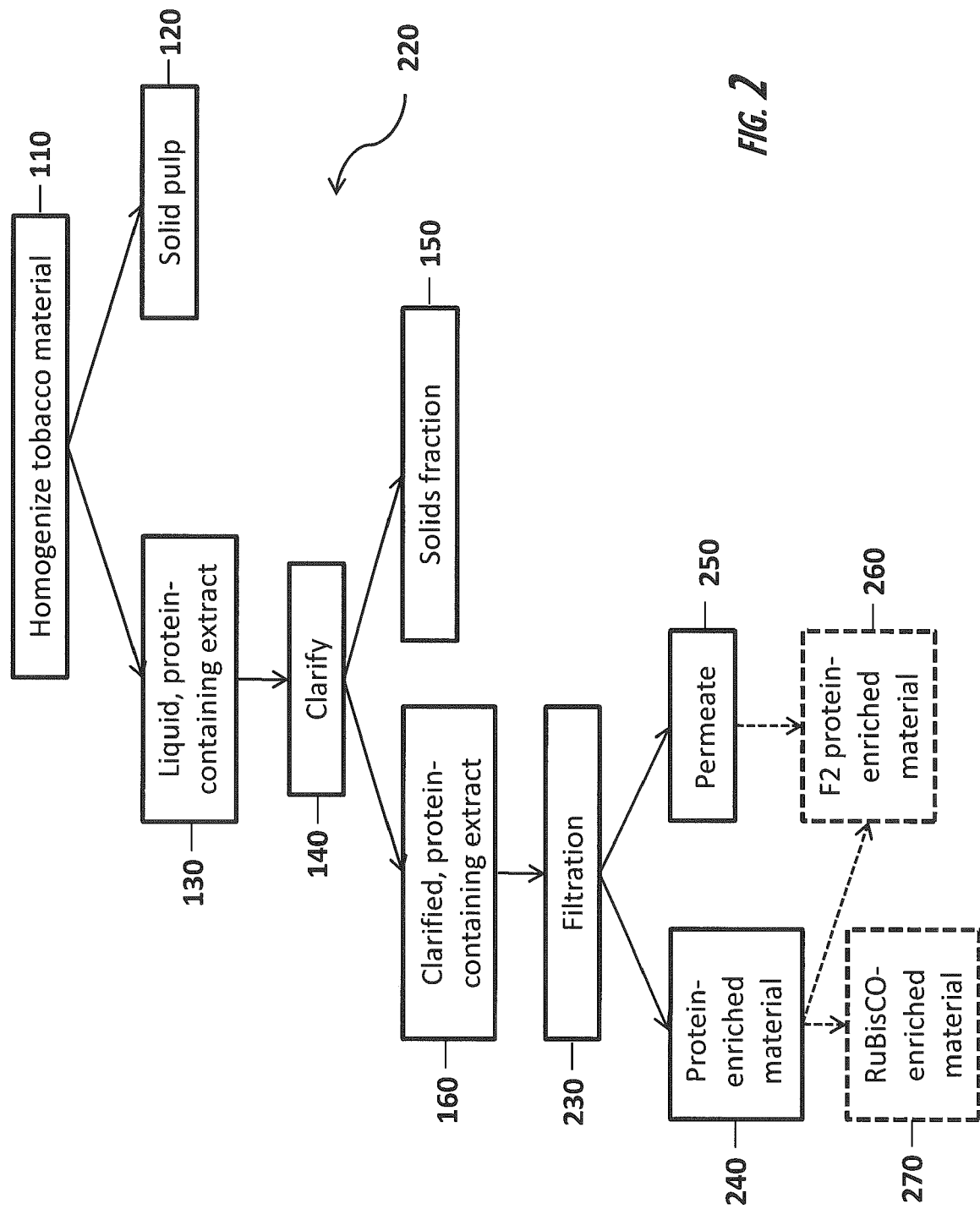
FIG. 2 is a schematic of a different process embodiment for the derivation of protein from a tobacco material.

An alternative process, 220, as shown in the embodiment illustrated in FIG. 2, for the production of a RuBisCO- and F2 protein-enriched material, RuBisCO-enriched material, and/or F2 protein-enriched material comprises the following steps. A tobacco material can be homogenized (110) to provide a solid pulp 120 and a liquid, protein-containing extract 130. Extract 130 is clarified (140) to remove solids therefrom, giving a solids fraction 150 and a clarified, protein-containing extract 160. Extract 160 is filtered (230) and washed to give a solid, RuBisCO-enriched material, 240 and a permeate, 250. In certain embodiments, the permeate may comprise F2 proteins and the permeate can optionally be processed to give an F2 protein-enriched material 260.

The steps and materials of FIG. 2 (i.e., step 110 through extract 160) can be conducted as described above in relation to the method of FIG. 1. It is preferable, according to the method shown in FIG. 2, that the clarification step 140 comprises a pH-adjustment step to provide an acidic or basic clarified, protein-containing extract. In the method of FIG. 2, the clarified, (acidic or basic), protein-containing extract 160 is subjected to filtration (230).

The process of filtration can comprise passing the liquid through one or more ceramic filters or semipermeable membranes to remove selected sizes of particulate matter (giving a retentate that remains on or in the filter material and a permeate that passes through the filter material) and/or components of the extract having a molecular weight above a certain threshold. The membrane can be of any type, such as plate-and-frame (having a stack of membranes and support plates), spiral-wound (having consecutive layers of membrane and support material rolled up around a tube), tubular (having a membrane-defined core through which the feed flows and an outer, tubular housing where permeate is collected), or hollow fiber (having several small diameter tubes or fibers wherein the permeate is collected in the cartridge area surrounding the fibers). The membrane can be constructed of any material. For example, polysulfone, polyethersulfone, polypropylene, polyvinylidenefluoride, and cellulose acetate membranes are commonly used, although other materials can be used without departing from the invention described herein. See, for example, the ultrafiltration techniques set forth in US Patent App. Publ. No. 2012/0152265 to Dube et al., which is incorporated by reference herein.

Ultrafiltration membranes are available in a wide range of pore sizes (typically ranging from about 0.1 to about 0.001 microns). Membranes are more typically described by their molecular weight cutoffs. Ultrafiltration membranes are commonly classified as membranes with number average molecular weight cutoffs of from about $10^3$ Da to about $10^5$ Da. In practice, compounds with molecular weights above the molecular weight cutoff are retained in the retentate, and the compounds with molecular weights below the cutoff pass through the filter into the permeate. Ultrafiltration methods typically are not capable of removing low molecular weight organic compounds and ions.

Ultrafiltration is typically a cross-flow separation process. The liquid stream to be treated (feed) flows tangentially along the membrane surface, separating into one stream that passes through the membrane (permeate) and another that does not (retentate or concentrate). The operating parameters of the ultrafiltration system can be varied to achieve the desired result. For example, the feed mixture to be filtered can be brought into contact with the membrane by way of applied pressure. The rate of permeation across the membrane is directly proportional to the applied pressure; however, the maximum pressure may be limited. The flow velocity of the mixture across the membrane surface can be adjusted. Temperature can also be varied. Typically, permeation rates increase with increasing temperature.

Commercial ultrafiltration systems are readily available and may be used for the ultrafiltration methods of the present invention. For example, commercial suppliers such as Millipore, Spectrum® Labs, Pall Corporation, Whatman®, Porex Corporation, and Snyder Filtration manufacture various filter membranes and cartridges, and/or filtration systems (e.g., tangential flow filtration systems). Exemplary membranes include, but are not limited to, Biomax® and Ultracel® membranes and Pellicon® XL cassettes (from Millipore), Microkros®, Minikros®, and KrosFlo® Hollow Fiber Modules (from Spectrum® Labs), and Microza filters and Centramate,™ Centrasette,™ Maximate™, and Maxisette™ Tangential Flow Filtration Membrane Cassettes. Commercially available filtration systems include, but are not limited to, Millipore's Labscale™ Tangential Flow Filtration (TFF) system and Spectrum® Labs' KrosFlo® and MiniKros® Tangential Flow Filtration Systems.

Filters and/or membranes that may be useful according to the present invention include those with molecular weight cutoffs of less than about 500,000 Da, less than about 250,000 Da, less than about 100,000 Da, less than about 75,000 Da, less than about 50,000 Da, less than about 25,000 Da, less than about 20,000 Da, less than about 15,000 Da, less than about 10,000 Da, less than about 5,000 Da, and about 1,000 Da. In certain embodiments, a multistage filtration process is used. Such embodiments employ multiple filters and/or membranes of different (typically decreasing) molecular weight cutoffs. Any number of filters and/or membranes can be used in succession according to the invention. For example, a first filtration may be conducted using a 500,000 Da molecular weight cutoff filter and a second filtration may be conducted using a 1,000 Da molecular weight cutoff filter although filters having various other MW cutoffs and/or pore sizes can be used. Further filtration means suitable for use in the various embodiments of the invention where filtration is desirable include those disclosed in U.S. Pat. No. 4,941,484 to Clapp et al., the disclosure of which is incorporated herein by reference in its entirety.

Following filtration, proteins are advantageously retained on the filtration membrane (or filter). The retentate is advantageously washed (e.g., with a glycine buffer or a histidine, sodium citrate, potassium phosphate or sodium phosphate solution) and can be dried (e.g., spray dried or frozen) to provide a protein-enriched material 240. The protein-enriched material 240 may, in some embodiments, be a RuBisCO-enriched material or a general protein-enriched material (comprising both RuBisCO and F2 fraction proteins). The specific membrane cutoffs can help to control the makeup of the protein-enriched product 240 provided according to method 220 of FIG. 2.

For example, in certain embodiments, filtration step 230 employs a 500 kDa ultrafiltration membrane, which can result in the separation of F1 (RuBisCO) from F2 proteins. RuBisCO generally does not pass through a 500 kDa ultrafiltration membrane, whereas F2 proteins do; accordingly, the retentate on a 500 kDa membrane should consist essentially of RuBisCO proteins, with little to no F2 proteins in the retentate. In such embodiments, the F2 proteins should be present in the permeate 250, which can optionally be further purified (e.g., via the removal of sugars, fats, and lipids) to give an F2 protein-enriched material 260. This further processing can, in some embodiments, consist of further ultrafiltration steps (e.g., passing permeate 250 through a 1 kDa membrane, a 10 kDa membrane, or a 20 kDa membrane) and drying the resulting retentate (e.g., by spray drying or freezing). In some embodiments, it may be unnecessary to dry the retentate, as it may be useful in certain embodiments in liquid or semi-solid form.

In certain embodiments, ultrafiltration step 230 employs a 1 kDa membrane, which generally maintains RuBisCO and F2 proteins together in the retentate, allowing other components of the extract (e.g., sugars, fats, and lipids) to pass through. The resulting solid retentate (protein-enriched material 240) in such embodiments will comprise a mixture of RuBisCO and F2 proteins. The ratio of Rubisco to F2 proteins can vary in the samples thus provided. Of course, it is to be understood that this mixture can be optionally further separated as provided herein if desired to separately provide a RuBisCO-enriched material and a F2 protein-enriched material. In certain embodiments, dissolving protein-enriched material 240 in a suitable solvent and passing it through a 500 kDa ultrafiltration membrane can result in the separation of F1 (RuBisCO) from F2 proteins, as the RuBisCO will be retained on the membrane and can be washed to give a RuBisCO-enriched material 270. The permeate can optionally be concentrated and dried to give F2 protein-enriched material 260.

The methods disclosed herein may, in some embodiments, provide a protein-enriched material, e.g., a material comprising at least about 50% protein by dry weight, at least about 60% protein by dry weight, at least about 70% protein by dry weight, at least about 80% protein by dry weight, at least about 90% protein by dry weight, at least about 95% protein by dry weight, at least about 98% protein by dry weight, or at least about 99% protein by dry weight. In some embodiments, the protein in the protein-enriched material comprises at least about 60% RuBisCO by dry weight, at least about 70% RuBisCO by dry weight, at least about 80% RuBisCO by dry weight, at least about 90% RuBisCO by dry weight, at least about 95% RuBisCO by dry weight, at least about 98% RuBisCO by dry weight, or at least about 99% RuBisCO by dry weight.

In some embodiments, the present disclosure specifically provides methods for the extraction and/or isolation of RuBisCO from a plant of the Nicotiana species or a portion thereof. Accordingly, the methods disclosed herein may, in some embodiments, provide a RuBisCO-enriched material, e.g., a material comprising at least about 50% RuBisCO by dry weight, at least about 60% RuBisCO by dry weight, at least about 70% RuBisCO by dry weight, at least about 80% RuBisCO by dry weight, at least about 90% RuBisCO by dry weight, at least about 95% RuBisCO by dry weight, at least about 98% RuBisCO by dry weight, or at least about 99% RuBisCO by dry weight. In some embodiments, the present disclosure further provides methods for the extraction and/or isolation of F2 proteins from a plant of the Nicotiana species or a portion thereof. Accordingly, the methods disclosed herein may, in some embodiments, provide an F2 protein-enriched material, e.g., a material comprising at least about 10% F2 protein by dry weight, at least about 20% F2 protein by dry weight, at least about 30% protein by dry weight, at least about 50% F2 protein by dry weight, at least about 60% F2 protein by dry weight, at least about 70% F2 protein by dry weight, at least about 80% F2 protein by dry weight, at least about 90% F2 protein by dry weight, at least about 95% F2 protein by dry weight, at least about 98% F2 protein by dry weight, or at least about 99% F2 protein by dry weight.

Although in some embodiments, the protein-enriched materials described herein can be used directly, it may be desirable to thermally treat the material in order to, for example, pasteurize the material or otherwise chemically alter the material. This thermal treatment can be conducted before or after any of the processes described herein (e.g., before or after any of the steps in process 100 of FIG. 1 and/or the steps in process 220 of FIG. 2) for the isolation of one or more components from a plant of the Nicotiana species. For example, a tobacco material can be thermally processed by mixing the tobacco material, water, and an additive selected from the group consisting of lysine, glycine, histidine, alanine, methionine, glutamic acid, aspartic acid, proline, phenylalanine, valine, arginine, di- and trivalent cations, asparaginase, saccharides, phenolic compounds, reducing agents, compounds having a free thiol group, oxidizing agents (e.g., hydrogen peroxide), oxidation catalysts, plant extracts, and combinations thereof, to form a moist tobacco mixture; and heating the moist tobacco mixture at a temperature of at least about 60° C. to form a heat-treated tobacco mixture. In one embodiment, the treated tobacco extract is heat treated in the presence of water, NaOH, and an additive (e.g., lysine) at about 88° C. for about 60 minutes. Such heat treatment can help prevent acrylamide production resulting from reaction of asparagine with reducing sugars in tobacco materials and can provide some degree of pasteurization. See, for example, US Pat. Pub. No. 2010/0300463 to Chen et al., which is incorporated herein by reference. In certain embodiments wherein a heat-treated tobacco-derived material is used in a smokeless tobacco product of the present invention, the product can be characterized by very low acrylamide content. For example, in some embodiments, the smokeless tobacco product is characterized by an acrylamide content of less than about 500 ppb (ng/g), less than about 400 ppb, less than about 300 ppb, less than about 200 ppb, or less than about 100 ppb. In some embodiments, in addition to or in place of the optional heat treatment, tobacco material can be irradiated (e.g., to ensure no microbes are associated with the treated protein-enriched material).

Following one or more of the methods disclosed herein for the isolation of one or more components from a plant of the *Nicotiana* species, any liquid material thus obtained can be further processed if desired. For example, the tobacco material can be subjected to further treatment steps, which can be used in the place of, or in addition to, the other isolation steps described herein. In some embodiments, the extract (e.g., liquid, protein containing extract 130, clarified, protein-containing extract 160, or permeate 250) is brought into contact with an imprinted polymer or non-imprinted polymer such as described, for example, in US Pat. Pub. Nos. 2007/0186940 to Bhattacharyya et al; 2011/0041859 to Rees et al.; and 2011/0159160 to Jonsson et al; and U.S. patent application Ser. No. 13/111,330 to Byrd et al., filed May 19, 2011, all of which are incorporated herein by reference. Treatment with a molecularly imprinted or non-imprinted polymer can be used to remove certain components of the extract, such as tobacco-specific nitrosamines (TSNAs), including N'-nitrosonornicotine (NNN), (4-methylnitrosamino)-1-(3-pyridyl)-1-butanone (NNK), N'-nitrosoanatabine (NAT), and N'-nitrosoanabasine (NAB); polyaromatic hydrocarbons (PAHs), including benz[a]anthracene, benzo[a]pyrene, benzo[b]fluoranthene, benzo[k]fluoranthene, chrysene, dibenz[a,h]anthracene, and indeno[1,2,3-cd]pyrene; or other Hoffmann analytes. In some embodiments, a molecularly imprinted or non-imprinted polymer can be used to remove nicotine from the extract.

In some embodiments, one or more of the materials (e.g., extracts or solids) described herein can be subjected to conditions so as to cause compounds contained in such materials to undergo chemical transformation. For example, the tobacco material obtained from plants of the *Nicotiana* species or portion thereof can be treated to cause chemical transformation or be admixed with other ingredients. In some embodiments, the tobacco-derived extracts (including liquid and solids fractions) obtained therefrom can be treated to cause chemical transformation or be admixed with other ingredients. The chemical transformations or modification of the tobacco material or extract thereof can result in changes of certain chemical and physical properties of the tobacco material or extract (e.g., the sensory attributes thereof). Exemplary chemical modification processes can be carried out by acid/base reaction, hydrolysis, oxidation, heating and/or enzymatic treatments; and as such, compounds can undergo various degradation reactions. Exemplary chemical transformation techniques are set forth in US Pat. Appl. Pub. Nos. 2011/0174323 to Coleman, III, et al. and 2011/0259353 to Coleman, III et al., which are incorporated by reference herein.

In certain embodiments, the tobacco material or extract thereof (including liquid and/or solid fractions) is treated to provide degradation products. Degradation products are any compounds that are produced from the compounds extracted and/or isolated according to the present invention. Degradation products can be formed naturally from such compounds or may be produced by an accelerated degradation process (e.g., by the addition of heat and/or chemicals to accelerate the breakdown of the compounds). These compounds can be degraded, for example, by means of oxidation (e.g., through treatment with $H_2O_2$ or other oxidizing agents) and/or hydrolysis reactions.

The form of the protein-enriched materials (i.e., RuBisCO-enriched material, combined RuBisCO/F2 protein-enriched material, and/or F2 protein-enriched material) obtained according to the methods of the present disclosure can vary. Typically, these materials are in solid, liquid, or semi-solid or gel forms. The resulting formulations can be used in concrete, absolute, or neat form. Solid forms of the tobacco-derived materials described herein can include spray-dried and freeze-dried forms. Liquid forms of the tobacco-derived materials described herein can include formulations contained within aqueous or organic solvent carriers.

Protein-enriched materials (i.e., RuBisCO-enriched material, combined RuBisCO protein-enriched/F2 protein-enriched material, and/or F2 protein-enriched material) are useful as materials for various compositions. For example, in some embodiments, the tobacco-derived materials described herein are incorporated within tobacco compositions, particularly tobacco compositions incorporated into smoking articles or smokeless tobacco products. In accordance with the present invention, a tobacco product incorporates tobacco that is combined with one or more of the tobacco-derived materials (i.e., RuBisCO-enriched material, combined RuBisCO/F2 protein-enriched material, and/or F2 protein-enriched material) according to the invention. That is, a portion of the tobacco product can be comprised of some form of protein-enriched tobacco material formulation prepared according to the present disclosure.

Addition of the tobacco-derived material or materials described herein to a tobacco composition can enhance a tobacco composition in a variety of ways, depending on the nature of the tobacco-derived material and the type of tobacco composition. Exemplary protein-enriched extracts, solids fractions, and combinations thereof can serve to provide flavor and/or aroma to a tobacco product (e.g., the composition can alter the sensory characteristics of tobacco compositions or smoke derived therefrom). Other protein-enriched extracts, solids fractions, and combinations thereof can serve functional purposes within tobacco compositions, such as binder or filler functions. Certain protein-enriched extracts, solids fractions, and combinations thereof can serve as a replacement for one or more traditional components of a tobacco product.

The tobacco product to which the tobacco-derived materials of the present disclosure are added can vary, and may include any product configured or adapted to deliver tobacco or some component thereof to the user of the product. Exemplary tobacco products include smoking articles (e.g., cigarettes), smokeless tobacco products, and aerosol-generating devices that contain nicotine and/or a tobacco material or other plant material that is not combusted during use. The incorporation of the protein-enriched, tobacco-derived materials of the invention into a tobacco product may involve use of a tobacco material or non-tobacco plant material as a carrier for the formulations, such as by absorbing the tobacco-derived, protein-enriched material (i.e., RuBisCO-enriched material, combined RuBisCO/F2 protein-enriched material, and/or F2 protein-enriched material) into the tobacco or other plant material or otherwise associating tobacco-derived, protein-enriched material with the carrier material. The types of tobacco that can serve as the carrier for the formulations of the invention can vary, and can include any of the tobacco types discussed herein, including various cured tobacco materials (e.g., flue-cured or air-cured tobaccos) or portions thereof (e.g., tobacco lamina or tobacco stems). The physical configuration of the tobacco material to which the formulation is added can also vary, and can include tobacco materials in shredded or particulate form, or in the form of a sheet (e.g., reconstituted tobacco sheets) or in whole leaf form.

Accordingly, protein-enriched, tobacco-derived materials provided herein can, in some embodiments, be used as compositions in the manufacture of smoking articles. For example, the formulations prepared in accordance with the present invention can be mixed with casing materials and applied to tobacco as a casing ingredient or as a top dressing. Still further, the formulations of the invention can be incorporated into a cigarette filter (e.g., in the filter plug, plug wrap, or tipping paper) or incorporated into cigarette wrapping paper, preferably on the inside surface, during the cigarette manufacturing process. See, for example, the description and references related to tobacco isolates used in smoking articles set forth in US Pat. Pub. No. 2012/0192880 to Dube et al., which is incorporated by reference herein. Representative tobacco blends, non-tobacco components, and representative cigarettes manufactured therefrom are also set forth in the Dube et al. reference noted above.

Figure 3:
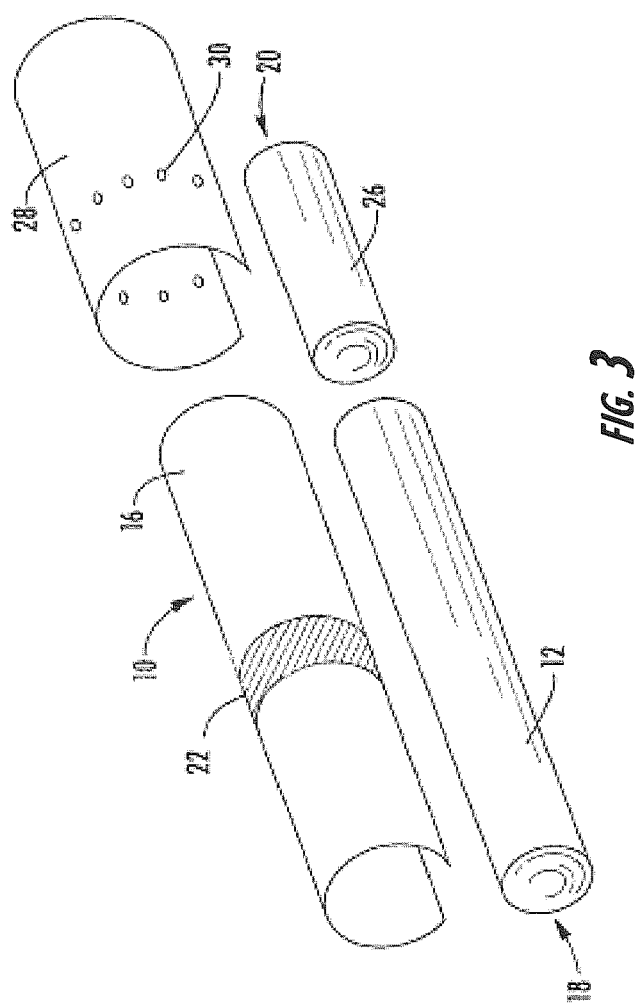
FIG. 3 is an exploded perspective view of a smoking article having the form of a cigarette, showing the smokable material, the wrapping material components, and the filter element of the cigarette.

Referring to FIG. 3, there is shown a smoking article 10 in the form of a cigarette and possessing certain representative components of a smoking article that can contain the formulation of the present invention. The cigarette 10 includes a generally cylindrical rod 12 of a charge or roll of smokable filler material (e.g., about 0.3 to about 1.0 g of smokable filler material such as tobacco material) contained in a circumscribing wrapping material 16. The rod 12 is conventionally referred to as a "tobacco rod." The ends of the tobacco rod 12 are open to expose the smokable filler material. The cigarette 10 is shown as having one optional band 22 (e.g., a printed coating including a film-forming agent, such as starch, ethylcellulose, or sodium alginate) applied to the wrapping material 16, and that band circumscribes the cigarette rod in a direction transverse to the longitudinal axis of the cigarette. The band 22 can be printed on the inner surface of the wrapping material (i.e., facing the smokable filler material), or less preferably, on the outer surface of the wrapping material.

At one end of the tobacco rod 12 is the lighting end 18, and at the mouth end 20 is positioned a filter element 26. The filter element 26 positioned adjacent one end of the tobacco rod 12 such that the filter element and tobacco rod are axially aligned in an end-to-end relationship, preferably abutting one another. Filter element 26 may have a generally cylindrical shape, and the diameter thereof may be essentially equal to the diameter of the tobacco rod. The ends of the filter element 26 permit the passage of air and smoke therethrough.

A ventilated or air diluted smoking article can be provided with an optional air dilution means, such as a series of perforations 30, each of which extend through the tipping material and plug wrap. The optional perforations 30 can be made by various techniques known to those of ordinary skill in the art, such as laser perforation techniques. Alternatively, so-called off-line air dilution techniques can be used (e.g., through the use of porous paper plug wrap and pre-perforated tipping paper). The formulations of the invention can be incorporated within any of the components of a smoking article, including but not limited to, as a component of the tobacco charge, as a component of the wrapping paper (e.g., included within the paper or coated on the interior or exterior of the paper), as an adhesive, as a filter element component, and/or within a capsule located in any region of the smoking article.

The formulations of the invention can also be incorporated into aerosol-generating devices that contain nicotine and/or tobacco material (or some portion or component thereof) that is not intended to be combusted during use, including so-called "e-cigarettes". Some of these types of smoking articles employ a combustible fuel source that is burned to provide an aerosol and/or to heat an aerosol-forming material. Others employ battery-powered heating elements to heat an aerosol-forming composition. Exemplary references that describe smoking articles of a type that generate flavored vapor, visible aerosol, or a mixture of flavored vapor and visible aerosol, include those set forth in US Pat. Pub. No. 2012/0192880 to Dube et al., which is incorporated by reference herein.

The formulations of the invention can be incorporated into smokeless tobacco products, such as loose moist snuff (e.g., snus); loose dry snuff; chewing tobacco; pelletized tobacco pieces; extruded or formed tobacco strips, pieces, rods, cylinders or sticks; finely divided ground powders; finely divided or milled agglomerates of powdered pieces and components; flake-like pieces; molded tobacco pieces; gums; rolls of tape-like films; readily water-dissolvable or water-dispersible films or strips; meltable compositions; lozenges; pastilles; or capsule-like materials possessing an outer shell and an inner region. Various types of smokeless tobacco products are described or referenced in US Pat. Pub. No 2012/0152265 to Dube et al., which is incorporated herein by reference.

Figure 4:
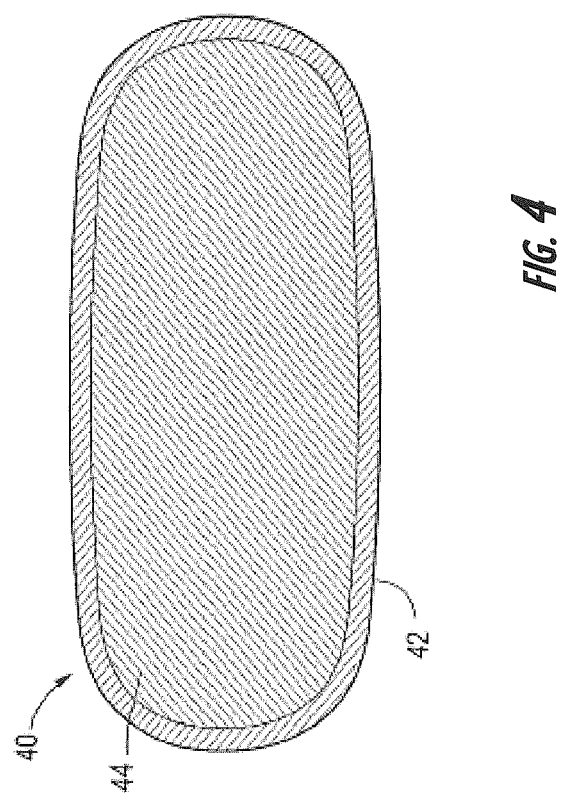
FIG. 4 is a cross-sectional view of a smokeless tobacco product embodiment, taken across the width of the product, showing an outer pouch filled with a smokeless tobacco composition of the invention.

Referring to FIG. 4, a representative snus type of tobacco product comprising a formulation of the present invention is shown. In particular, FIG. 4 illustrates a smokeless tobacco product 40 having a water-permeable outer pouch 42 containing a smokeless tobacco composition 44. Any of the components of the tobacco product can comprise a tobacco-derived material as described herein (e.g., the interior or exterior of the pouch lining or a portion of the smokeless tobacco composition contained therein).

Many exemplary smokeless tobacco compositions that can benefit from use of the formulations of the invention comprise shredded or particulate tobacco material that can serve as a carrier for the protein-enriched, tobacco-derived materials of the invention. The smokeless tobacco compositions of the invention can also include a water-soluble polymeric binder material and optionally other ingredients that provide a dissolvable composition that will slowly disintegrate in the oral cavity during use. In certain embodiments, the smokeless tobacco composition can include lipid components that provide a meltable composition that melts (as opposed to merely dissolving) in the oral cavity, such as compositions set forth in US Pat. Pub. No. 2012/0037175 to Cantrell et al., which is incorporated by reference herein.

In one particular smokeless tobacco product embodiment, a composition of the invention is added to a non-tobacco plant material, such as a plant material selected from potato, beet (e.g., sugar beet), grain, pea, apple, and the like. The non-tobacco plant material can be used in a processed form. In certain preferred embodiments, the non-tobacco plant material can be used in an extracted form, and as such, at least a portion of certain solvent soluble components are removed from that material. The non-tobacco extracted plant material is typically highly extracted, meaning a substantial amount of the aqueous soluble portion of the plant material has been removed. See, for example, US Pat. Pub. No. 2011/0247640 to Beeson et al, which is incorporated by reference herein.

Further ingredients can be admixed with, or otherwise incorporated within, the smokeless tobacco compositions according to the invention. The ingredients can be artificial, or can be obtained or derived from herbal or biological sources. Exemplary types of ingredients include salts (e.g., sodium chloride, potassium chloride, sodium citrate, potassium citrate, sodium acetate, potassium acetate, and the like), natural sweeteners (e.g., fructose, sucrose, glucose, maltose, vanillin, ethylvanillin glucoside, mannose, galactose, lactose, and the like), artificial sweeteners (e.g., sucralose, saccharin, aspartame, acesulfame K, neotame and the like), organic and inorganic fillers (e.g., grains, processed grains, puffed grains, maltodextrin, dextrose, calcium carbonate, calcium phosphate, corn starch, lactose, manitol, xylitol, sorbitol, finely divided cellulose, and the like), binders (e.g., povidone, sodium carboxymethylcellulose and other modified cellulosic types of binders, sodium alginate, xanthan gum, starch-based binders, gum arabic, lecithin, and the like), pH adjusters or buffering agents (e.g., metal hydroxides, preferably alkali metal hydroxides such as sodium hydroxide and potassium hydroxide, and other alkali metal buffers such as metal carbonates, preferably potassium carbonate or sodium carbonate, or metal bicarbonates such as sodium bicarbonate, and the like), colorants (e.g., dyes and pigments, including caramel coloring and titanium dioxide, and the like), humectants (e.g., glycerin, propylene glycol, and the like), effervescing materials such as certain acid/base combinations, oral care additives (e.g., thyme oil, eucalyptus oil, and zinc), preservatives (e.g., potassium sorbate, and the like), syrups (e.g., honey, high fructose corn syrup, and the like), disintegration aids (e.g., microcrystalline cellulose, croscarmellose sodium, crospovidone, sodium starch glycolate, pregelatinized corn starch, and the like), flavorant and flavoring mixtures, antioxidants, and mixtures thereof. Exemplary encapsulated additives are described, for example, in WO 2010/132444 to Atchley, which has been previously incorporated by reference herein. See also, the smokeless tobacco ingredients set forth in US Pat. Pub. Nos. 2012/0055494 to Hunt et al. and 2012/0199145 to Byrd et al., which are incorporated by reference herein.

The amount of the protein-enriched, tobacco-derived materials of the present invention incorporated within a tobacco composition or tobacco product can depend on the desired function of the protein-enriched, tobacco-derived material, the chemical makeup of the protein-enriched, tobacco-derived material, and the type of tobacco composition to which the protein-enriched, tobacco-derived material is added. The amount of protein-enriched, tobacco-derived material added to a tobacco composition can vary, but will typically not exceed about 50 weight percent based on the total dry weight of the tobacco composition to which the composition is added. For example, the amount of protein-enriched, tobacco-derived material added to a tobacco composition may be in the range of about 0.25 to about 25 weight percent or about 1 to about 10 weight percent, based on the total dry weight of the tobacco composition.

Although the use of such protein-enriched, tobacco-derived materials is generally described in the context of tobacco compositions, it is noted that such formulations can be applicable in many other types of compositions. For example, protein-enriched tobacco materials of the invention can be used in foods or beverages or otherwise incorporated into a dietary supplement intended for oral consumption, such as dietary supplements as defined by the Dietary Supplement Health and Education Act of 1994 (DSHEA). Protein-enriched tobacco materials can also be incorporated into foods designed specifically for animals (e.g., pet foods). Additional uses include cosmetic and pharmaceutical compositions.

Protein-containing dietary supplements of the invention can take various forms, including powders, liquids, bars, and the like. Such supplements typically include additional components and excipients such as sweeteners, fillers, colorants, antioxidants, vitamins, minerals, and the like. The protein-enriched materials of the invention could be used, for example, in the compositions and formulations set forth in US Pat. Pub. Nos. 2006/0280840 to Robertson; 2008/0268095 to Herzog; 2009/0317530 to Rotem et al.; 2011/0020501 to Verbiest et al.; 2011/0245158 to Scheele; 2012/0064058 to Cavallo et al.; 2012/0301599 to Hoijer et al.; and 2013/0046018 to Romero et al., all of which are incorporated by reference herein.

EXPERIMENTAL

Aspects of the present invention is more fully illustrated by the following examples, which are set forth to illustrate certain aspects of the present invention and are not to be construed as limiting thereof.

Example 1—Acidic Clarification and Precipitation to Obtain RuBisCO

Tobacco plants are harvested, leaves are stripped from the stalks, and the leaves are homogenized in a disintegrator by adding water thereto and the material is then passed into a horizontal screw press for liquid extraction. The liquid protein-containing extract thus obtained is a green juice having a pH of 8.6. This protein-containing extract is clarified first by passing the extract through a decanter. The pH of the protein-containing extract is adjusted to 5.9 using hydrochloric acid. Diatomaceous earth is optionally added to the extract, the mixture is stirred for 15 minutes, and then passed through a filter press.

The resulting clarified, protein-containing extract is treated with citric acid and hydrochloric acid to adjust the pH to 4.92. The pH-adjusted extract is left to sit for 47 hours. Liquid is decanted from the top of the mixture and a settled solid at the bottom of the mixture is obtained and processed on a 1.4 µm ceramic filter using tangential flow filtration. The retentate therefrom is concentrated to give a protein-enriched tobacco-derived material. The materials thus obtained comprise between about 85 and about 99% protein by weight.

Example 2—Acidic Clarification to Obtain RuBisCO

Tobacco plants are harvested, leaves are stripped from the stalks, and the leaves are homogenized in a disintegrator by adding water thereto and the material is then passed into a horizontal screw press for liquid extraction. The liquid protein-containing extract thus obtained is a green juice having a pH of 8.4. This protein-containing extract is clarified first by passing the extract through a decanter. The pH of the protein-containing extract is adjusted to 5.9 using hydrochloric acid. Diatomaceous earth is optionally added to the extract, the mixture is stirred for 15 minutes, and then passed through a filter press. The filtrate is washed with water, pH adjusted to 5.9 to increase recovery of protein.

The resulting clarified, protein-containing extract is processed on a 500 kDa reverse osmosis filter using tangential flow filtration. The retentate is washed with a glycine solution (75 mM glycine at pH 10.5) to give a RuBisCO-enriched tobacco-derived material retentate (comprising about 75-85% protein by weight). The permeate is cooled to 8° C. and processed on a 1 kDa reverse osmosis filter using tangential flow filtration. The 1 kDa retentate is washed with the glycine solution and concentrated to give a F2 protein-enriched tobacco-derived material (comprising about 30-40% F2 protein, although higher percentages, e.g., 65% have been obtained using alternate filtration methods, e.g., using 10 kDa and/or 20 kDa filters in place of the 1 kDa filter).

Example 3—Acidic Clarification and Precipitation to Obtain RuBisCO

Tobacco plants are harvested, leaves are stripped from the stalks, and the leaves are homogenized in a disintegrator by adding water thereto and the material is then passed into a horizontal screw press for liquid extraction. The liquid protein-containing extract thus obtained is a green juice having a pH of 8.7. This protein-containing extract is clarified first by passing the extract through a decanter. The pH of the protein-containing extract is adjusted to 5.9 using hydrochloric acid. Diatomaceous earth is added to the extract, the mixture is stirred for 15 minutes, and then passed through a filter press.

The resulting clarified, protein-containing extract is treated with hydrochloric acid to adjust the pH to 4.98. The pH-adjusted extract is left to sit for 60 hours. Liquid is decanted from the top of the mixture and a settled solid at the bottom of the mixture is obtained and processed on a 1.4 μm ceramic filter using tangential flow filtration. The retentate therefrom is concentrated to give a protein-enriched tobacco-derived material. The materials thus obtained comprise between about 85 and about 99% protein by weight.

Example 4—Basic Clarification to Obtain RuBisCO and F2 Fractions

Tobacco plants are harvested, leaves are stripped from the stalks, and the leaves are homogenized in a disintegrator by adding water thereto and the material is then passed into a horizontal screw press for liquid extraction. The liquid protein-containing extract thus obtained is a green juice having a pH of 8.5. This protein-containing extract is clarified first by passing the extract through a decanter. The pH of the protein-containing extract is adjusted to 10.5 using sodium hydroxide. Activated carbon is added and diatomaceous earth is added to the extract, the mixture is stirred for 15 minutes, and then brought into contact with a filter press. As the mixture was not passing through the filter press, the pH of the mixture is adjusted to 5.9 using hydrochloric acid and then passes through the filter press.

The resulting clarified, protein-containing permeate is processed on a 500 kDa reverse osmosis filter using tangential flow filtration. The retentate is washed with a glycine solution (75 mM glycine at pH 10.5), giving a RuBisCO protein-containing retentate (comprising about 75-85% protein by weight) and stored. The permeate is cooled to 8° C. and processed on a 1 kDa reverse osmosis filter using tangential flow filtration. The retentate is washed with the glycine solution and concentrated to give a F2 fraction protein-enriched tobacco-derived material (comprising about 30-40% F2 protein, although higher percentages, e.g., 65% have been obtained using alternate filtration methods, e.g., using 10 kDa and/or 20 kDa filters in place of the 1 kDa filter).

Example 5—Acidic Clarification to Obtain RuBisCO and F2 Fractions

Tobacco plants are harvested, leaves are stripped from the stalks, and the leaves are homogenized in a disintegrator by adding water thereto and the material is then passed into a horizontal screw press for liquid extraction. The liquid protein-containing extract thus obtained is a green juice having a pH of 8.4. This protein-containing extract is clarified first by passing the extract through a decanter. The pH of the protein-containing extract is adjusted to 5.9 using hydrochloric acid. Activated carbon is added and diatomaceous earth is added to the extract, the mixture is stirred for 15 minutes, and then passed through a filter press. The resulting clarified, protein-containing permeate is processed on a 500 kDa reverse osmosis filter using tangential flow filtration. The retentate is washed with a glycine solution (75 mM glycine at pH 10.5), giving RuBisCO protein-containing retentate (comprising about 75-85% protein by weight), which is stored. The permeate is cooled to 8° C. and processed on a 1 kDa reverse osmosis filter using tangential flow filtration. The retentate is washed with the glycine solution and concentrated to give a F2 fraction protein-enriched tobacco-derived material (comprising about 30-40% F2 protein, although higher percentages, e.g., 65% have been obtained using alternate filtration methods, e.g., using 10 kDa and/or 20 kDa filters in place of the 1 kDa filter).

Example 6—Isolation of Combined RuBisCO and F2 Proteins and Subsequent Separation Tobacco plants are harvested, chipped, and homogenized in a disintegrator by adding water thereto and the material is then passed into a horizontal screw press for liquid extraction. The liquid protein-containing extract thus obtained is a green juice having a pH of 5.6. The pH of the protein-containing extract is adjusted to 7.10 using sodium hydroxide. Diatomaceous earth is added to the extract, the mixture is stirred for 15 minutes, and then passed through a filter press. The resulting clarified, protein-containing permeate is processed on a 1 kDa filter using tangential flow filtration. The retentate comprises a mixture of RuBisCO and F2 proteins and comprises approximately 50% protein.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed:

1. A method for obtaining a protein-enriched material from a plant of the *Nicotiana* species or portion thereof, comprising:

receiving a plant material of the *Nicotiana* species;

contacting the plant material with a solvent for a time and under conditions sufficient to extract one or more proteins from the plant material into the solvent and form a liquid protein-containing extract;

separating a solid extracted plant material from the liquid protein-containing extract;

clarifying the liquid protein-containing extract to form a clarified protein-containing extract and a solids fraction; and treating the clarified protein-containing extract so as to provide a protein-enriched material comprising at least about 60% protein by dry weight, wherein the treating step comprises filtering the clarified protein-containing extract to give a retentate and a liquid permeate; and washing the retentate to provide the protein-enriched material, wherein the treating step comprises filtering the clarified protein-containing extract through a microfiltration membrane, and wherein the microfiltration membrane has a pore size of about 0.05 to about 10 microns and wherein the retentate comprises at least about 50% RuBisCO by dry weight.

2. The method of claim 1, wherein the protein-enriched material comprises at least about 80% protein by dry weight.

3. The method of claim 1, wherein the clarifying step comprises adjusting the pH of the liquid protein-containing extract.

4. The method of claim 1, wherein plant material of the *Nicotiana* species is in the form of a green plant material, yellowed plant material, cured plant material, or a mixture thereof.

5. The method of claim 1, further comprising spray drying, freeze drying, or otherwise dehydrating the protein-enriched material.

6. The method of claim 1, further comprising adding one or more components to remove color, odor, taste, alkaloids, metals, or a combination thereof, at any step of the process.

7. The method of claim 6, wherein the one or more components are selected from the group consisting of activated carbon, a resin, clay, a chelating agent, a molecularly imprinted polymer, a non-imprinted polymer, or a combination thereof.

8. The method of claim 1, further comprising:
filtering the liquid permeate through a 1 kDa membrane, a 10 kDa membrane, or a 20 kDa membrane, giving a membrane permeate comprising F2 protein.

9. The method of claim 8, further comprising concentrating the membrane permeate to give a membrane permeate comprising at least about 10% F2 protein by weight.

10. The method of claim 9, wherein the membrane permeate comprises at least about 30% F2 protein by weight.

11. The method of claim 9, further comprising distillation of the membrane permeate.

* * * * *